(12) United States Patent
Hebert

(10) Patent No.: US 9,549,666 B2
(45) Date of Patent: Jan. 24, 2017

(54) COAXIAL MICRO-ENDOSCOPE

(71) Applicant: Stephen J. Hebert, San Francisco, CA (US)

(72) Inventor: Stephen J. Hebert, San Francisco, CA (US)

(73) Assignee: Curvo Medical, Inc., San Francisco, CA (US)

( * ) Notice: Subject to any disclaimer, the term of this patent is extended or adjusted under 35 U.S.C. 154(b) by 431 days.

(21) Appl. No.: 14/064,171

(22) Filed: Oct. 27, 2013

(65) Prior Publication Data
US 2014/0135576 A1    May 15, 2014

Related U.S. Application Data

(60) Provisional application No. 61/724,922, filed on Nov. 10, 2012.

(51) Int. Cl.
*A61B 1/00* (2006.01)
*A61B 1/005* (2006.01)
*A61B 1/012* (2006.01)

(52) U.S. Cl.
CPC .......... *A61B 1/0057* (2013.01); *A61B 1/0055* (2013.01); *A61B 1/012* (2013.01)

(58) Field of Classification Search
CPC ....... A61B 1/008; A61B 1/012; A61B 1/0055; A61B 1/0057; A61B 1/005
See application file for complete search history.

(56) References Cited

U.S. PATENT DOCUMENTS

| 4,723,936 A | 2/1988 | Buchbinder et al. |
| 4,739,786 A | 4/1988 | Parkinson |
| 4,927,413 A | 5/1990 | Hess |
| 4,940,062 A | 7/1990 | Hampton et al. |
| 4,960,134 A | 10/1990 | Webster, Jr. |
| 5,152,744 A | 10/1992 | Krause |
| 5,169,568 A | 12/1992 | Ainger, III |
| 5,199,417 A | 4/1993 | Muller et al. |

(Continued)

FOREIGN PATENT DOCUMENTS

| CN | 101433469 | 5/2009 |
| EP | 1346747 | 9/2003 |

(Continued)

OTHER PUBLICATIONS

PCT/US2013/069435 International Search Report (Nov. 11, 2013).

(Continued)

*Primary Examiner* — Kristen Matter

(57) ABSTRACT

A deflectable endoscope including an imaging structure, an outer member having a proximal portion and a distal portion, an elongated column member extending distally from the outer member and an inner member positioned coaxial with the outer member and attached to the column member. The inner member extends distally of the outer member and has a distal tip portion. A reinforcement member is positioned over the column member to restrict axial movement of the column member such that when one of the inner member or outer member is moved with respect to the other, axial compression of the column member is restricted by the reinforcement member causing the distal tip portion of the inner member to deflect laterally.

18 Claims, 19 Drawing Sheets

(56) References Cited

U.S. PATENT DOCUMENTS

| | | | |
|---|---|---|---|
| 5,325,845 A | 7/1994 | Adair | |
| 5,383,923 A | 1/1995 | Webster, Jr. | |
| 5,396,880 A * | 3/1995 | Kagan | A61B 1/0051 600/109 |
| 5,431,168 A | 7/1995 | Webster, Jr. | |
| 5,441,483 A | 8/1995 | Avitall | |
| 5,470,330 A | 11/1995 | Goldenberg et al. | |
| 5,480,382 A * | 1/1996 | Hammerslag | A61M 25/0053 600/585 |
| 5,484,433 A | 1/1996 | Taylor et al. | |
| 5,562,619 A | 10/1996 | Mirarchi et al. | |
| 5,611,777 A | 3/1997 | Bowden et al. | |
| 5,632,734 A | 5/1997 | Galel et al. | |
| 5,715,832 A | 2/1998 | Koblish et al. | |
| 5,820,592 A | 10/1998 | Hammerslag | |
| 5,853,368 A * | 12/1998 | Solomon | A61B 8/12 600/439 |
| 5,921,978 A | 7/1999 | Thompson et al. | |
| 6,083,222 A | 7/2000 | Klein et al. | |
| 6,092,526 A | 7/2000 | LaFontaine et al. | |
| 6,096,022 A | 8/2000 | Laymon et al. | |
| 6,123,699 A | 9/2000 | Webster, Jr. | |
| 6,493,575 B1 | 12/2002 | Kesten et al. | |
| 6,500,167 B1 | 12/2002 | Webster, Jr. | |
| 6,527,769 B2 | 3/2003 | Langberg et al. | |
| 6,554,794 B1 | 4/2003 | Mueller et al. | |
| 6,572,593 B1 | 6/2003 | Daum | |
| 6,640,120 B1 | 10/2003 | Swanson et al. | |
| 6,671,550 B2 | 12/2003 | Iaizzo et al. | |
| 6,726,700 B1 | 4/2004 | Levine | |
| 6,733,500 B2 | 5/2004 | Kelley et al. | |
| 6,743,227 B2 | 6/2004 | Seraj et al. | |
| 6,778,846 B1 | 8/2004 | Martinez et al. | |
| 6,836,687 B2 | 12/2004 | Kelley et al. | |
| 6,893,436 B2 | 5/2005 | Woodard et al. | |
| 6,926,711 B2 | 8/2005 | Lentz et al. | |
| 6,936,047 B2 | 8/2005 | Nasab et al. | |
| 6,951,554 B2 | 10/2005 | Johansen et al. | |
| 7,027,851 B2 | 4/2006 | Mejia | |
| 7,039,450 B2 | 5/2006 | Duarte | |
| 7,089,063 B2 | 8/2006 | Lesh et al. | |
| 7,099,717 B2 | 8/2006 | Woodard et al. | |
| 7,252,664 B2 | 8/2007 | Nasab et al. | |
| 7,481,778 B2 | 1/2009 | Cedro et al. | |
| 7,497,844 B2 | 3/2009 | Spear et al. | |
| 7,507,205 B2 | 3/2009 | Borovsky et al. | |
| 7,565,208 B2 | 7/2009 | Harris et al. | |
| 7,569,626 B2 | 8/2009 | Truckai et al. | |
| 7,591,813 B2 | 9/2009 | Levine et al. | |
| 7,615,032 B2 | 11/2009 | Whittaker et al. | |
| 7,615,044 B2 | 11/2009 | Scheibe et al. | |
| 7,641,480 B1 | 1/2010 | Hossack et al. | |
| 7,648,517 B2 | 1/2010 | Makower et al. | |
| 7,674,253 B2 | 3/2010 | Fisher et al. | |
| 7,694,683 B2 | 4/2010 | Callister et al. | |
| 7,699,829 B2 | 4/2010 | Harris et al. | |
| 7,717,853 B2 | 5/2010 | Nita | |
| 7,731,681 B2 | 6/2010 | Schaer et al. | |
| 7,736,346 B2 | 6/2010 | Miller et al. | |
| 7,766,868 B2 | 8/2010 | Goode et al. | |
| 7,766,961 B2 | 8/2010 | Patel et al. | |
| 7,771,388 B2 | 8/2010 | Olsen et al. | |
| 7,794,454 B2 | 9/2010 | Abboud et al. | |
| 7,815,577 B2 | 10/2010 | Krishnan | |
| 7,818,040 B2 | 10/2010 | Spear et al. | |
| 7,824,517 B2 | 11/2010 | Kampa et al. | |
| 7,867,194 B2 | 1/2011 | Fiering et al. | |
| 7,881,769 B2 | 2/2011 | Sobe | |
| 7,909,797 B2 | 3/2011 | Kennedy, II et al. | |
| 7,914,503 B2 | 3/2011 | Goodson, IV et al. | |
| 7,918,819 B2 | 4/2011 | Karmarkar et al. | |
| 7,922,650 B2 | 4/2011 | McWeeney et al. | |
| 7,922,654 B2 | 4/2011 | Boutillette et al. | |
| 7,942,850 B2 | 5/2011 | Levit et al. | |
| 7,967,830 B2 | 6/2011 | Ayala et al. | |
| 7,976,528 B2 | 7/2011 | Nash et al. | |
| 7,988,646 B2 | 8/2011 | Taber | |
| 7,998,112 B2 | 8/2011 | Chow | |
| 8,075,498 B2 | 12/2011 | Leo et al. | |
| 8,118,803 B1 | 2/2012 | Chow et al. | |
| 8,147,481 B2 | 4/2012 | Whittaker et al. | |
| 8,152,799 B2 | 4/2012 | Ormsby et al. | |
| 8,172,828 B2 | 5/2012 | Chang et al. | |
| 8,172,829 B2 | 5/2012 | Farnholtz | |
| 8,195,297 B2 | 6/2012 | Penner | |
| 8,206,320 B2 | 6/2012 | Deal et al. | |
| 8,211,011 B2 | 7/2012 | Whayne et al. | |
| 8,211,087 B2 | 7/2012 | Carter et al. | |
| 8,211,171 B2 | 7/2012 | Kim et al. | |
| 8,213,075 B2 | 7/2012 | Chui et al. | |
| 8,214,018 B2 | 7/2012 | Markowitz et al. | |
| 8,216,224 B2 | 7/2012 | Morris et al. | |
| 8,216,256 B2 | 7/2012 | Raschdorf, Jr. et al. | |
| 8,216,277 B2 | 7/2012 | Zucherman et al. | |
| 8,216,281 B2 | 7/2012 | Winslow et al. | |
| 8,220,466 B2 | 7/2012 | Frazier et al. | |
| 8,220,487 B2 | 7/2012 | Unger et al. | |
| 8,220,494 B2 | 7/2012 | Studer et al. | |
| 8,221,396 B2 | 7/2012 | Dehnad et al. | |
| 8,221,402 B2 | 7/2012 | Francischelli et al. | |
| 8,221,463 B2 | 7/2012 | Zucherman et al. | |
| 8,222,023 B2 | 7/2012 | Battrell et al. | |
| 8,224,422 B2 | 7/2012 | Mottola et al. | |
| 8,224,438 B2 | 7/2012 | Levin | |
| 8,226,246 B2 | 7/2012 | Shirai et al. | |
| 8,228,593 B2 | 7/2012 | Shirai et al. | |
| 8,228,594 B2 | 7/2012 | Shirai et al. | |
| 8,231,613 B2 | 7/2012 | Baxter et al. | |
| 8,231,639 B2 | 7/2012 | Bolduc et al. | |
| 8,234,824 B2 | 8/2012 | Botkin et al. | |
| 8,235,047 B2 | 8/2012 | Swann et al. | |
| 8,235,468 B2 | 8/2012 | Fookes et al. | |
| 8,235,997 B2 | 8/2012 | Hoffman et al. | |
| 8,236,033 B2 | 8/2012 | Paul | |
| 8,238,013 B2 | 8/2012 | Ichikawa et al. | |
| 8,238,019 B2 | 8/2012 | Endo et al. | |
| 8,239,001 B2 | 8/2012 | Verard et al. | |
| 8,241,494 B2 | 8/2012 | Assion | |
| 8,247,178 B2 | 8/2012 | McBride et al. | |
| 8,256,585 B2 | 9/2012 | Halford et al. | |
| 8,256,628 B2 | 9/2012 | Stafford et al. | |
| 8,257,369 B2 | 9/2012 | Gellman et al. | |
| 8,257,397 B2 | 9/2012 | Winslow et al. | |
| 8,260,399 B2 | 9/2012 | Karmarkar et al. | |
| 8,267,979 B2 | 9/2012 | Flynn et al. | |
| 8,268,446 B2 | 9/2012 | Desimone et al. | |
| 8,270,061 B2 | 9/2012 | Endo et al. | |
| 8,271,069 B2 | 9/2012 | Jascob et al. | |
| 8,273,073 B2 | 9/2012 | Levine et al. | |
| 8,273,086 B2 | 9/2012 | Serhan et al. | |
| 8,273,107 B2 | 9/2012 | Zucherman et al. | |
| 8,273,241 B2 | 9/2012 | Feldman et al. | |
| 8,273,574 B2 | 9/2012 | Quake et al. | |
| 8,323,241 B2 | 12/2012 | Salahieh et al. | |
| 8,388,572 B2 | 3/2013 | Olsen et al. | |
| 8,920,369 B2 | 12/2014 | Salahieh et al. | |
| 9,174,022 B2 | 11/2015 | Uihlein | |
| 2002/0068924 A1 | 6/2002 | Sinofsky | |
| 2002/0072712 A1 | 6/2002 | Nool et al. | |
| 2002/0161330 A1 | 10/2002 | Nguyen | |
| 2003/0114844 A1 | 6/2003 | Ormsby et al. | |
| 2004/0097804 A1 | 5/2004 | Sobe | |
| 2004/0116851 A1 | 6/2004 | Johansen et al. | |
| 2004/0176741 A1 | 9/2004 | Farnholtz | |
| 2004/0225256 A1 | 11/2004 | Ponzi et al. | |
| 2005/0010237 A1 | 1/2005 | Niazi | |
| 2005/0020914 A1 | 1/2005 | Amundson et al. | |
| 2005/0054976 A1 | 3/2005 | Goode et al. | |
| 2005/0070794 A1 | 3/2005 | Deal et al. | |
| 2005/0070821 A1 | 3/2005 | Deal et al. | |
| 2005/0143770 A1 | 6/2005 | Carter et al. | |
| 2005/0187519 A1 | 8/2005 | Harris et al. | |
| 2005/0222557 A1 | 10/2005 | Baxter et al. | |
| 2005/0222558 A1 | 10/2005 | Baxter et al. | |

(56) References Cited

U.S. PATENT DOCUMENTS

| | | |
|---|---|---|
| 2005/0234436 A1 | 10/2005 | Baxter et al. |
| 2005/0234437 A1 | 10/2005 | Baxter et al. |
| 2005/0273020 A1 | 12/2005 | Whittaker et al. |
| 2006/0025705 A1 | 2/2006 | Whittaker et al. |
| 2006/0030864 A1 | 2/2006 | Kennedy II et al. |
| 2006/0142732 A1 | 6/2006 | Karmarkar et al. |
| 2006/0167418 A1 | 7/2006 | Khayal et al. |
| 2006/0265043 A1 | 11/2006 | Mandrusov et al. |
| 2006/0282151 A1 | 12/2006 | Weber |
| 2007/0060847 A1 | 3/2007 | Leo et al. |
| 2007/0156114 A1 | 7/2007 | Worley et al. |
| 2007/0156131 A1 | 7/2007 | Datta |
| 2007/0156133 A1 | 7/2007 | McDaniel et al. |
| 2007/0282303 A1 | 12/2007 | Nash et al. |
| 2008/0009745 A1 | 1/2008 | Hossack et al. |
| 2008/0086047 A1 | 4/2008 | McDaniel et al. |
| 2008/0097499 A1 | 4/2008 | Nash et al. |
| 2008/0167524 A1 | 7/2008 | Goldwasser et al. |
| 2008/0172037 A1 | 7/2008 | Huang et al. |
| 2008/0208240 A1 | 8/2008 | Paz |
| 2008/0234547 A1 | 9/2008 | Irion et al. |
| 2008/0234661 A1 | 9/2008 | Hastings et al. |
| 2008/0275536 A1 | 11/2008 | Zarins et al. |
| 2008/0287945 A1 | 11/2008 | Schaer |
| 2008/0312712 A1 | 12/2008 | Penner |
| 2008/0312725 A1 | 12/2008 | Penner |
| 2009/0005754 A1 | 1/2009 | Soetermans |
| 2009/0043299 A1 | 2/2009 | Racz |
| 2009/0099420 A1* | 4/2009 | Woodley ............ A61B 1/0053 600/142 |
| 2009/0105814 A1 | 4/2009 | Groothuis et al. |
| 2009/0105815 A1 | 4/2009 | Krever et al. |
| 2009/0105816 A1 | 4/2009 | Olsen et al. |
| 2009/0137953 A1 | 5/2009 | Fischer et al. |
| 2009/0149848 A1 | 6/2009 | Werneth et al. |
| 2009/0163822 A1 | 6/2009 | Doan |
| 2009/0171278 A1 | 7/2009 | Hirszowicz et al. |
| 2010/0004627 A1 | 1/2010 | Ludwig et al. |
| 2010/0030114 A1 | 2/2010 | Nguyen et al. |
| 2010/0057037 A1 | 3/2010 | Webler |
| 2010/0063478 A1 | 3/2010 | Selkee |
| 2010/0076408 A1 | 3/2010 | Krever et al. |
| 2010/0094334 A1 | 4/2010 | Krever et al. |
| 2010/0164137 A1 | 7/2010 | Selkee |
| 2010/0168666 A1 | 7/2010 | Tegg |
| 2010/0198049 A1 | 8/2010 | Karmarkar et al. |
| 2010/0204560 A1 | 8/2010 | Salahieh et al. |
| 2010/0217261 A1 | 8/2010 | Watson |
| 2010/0226903 A1 | 9/2010 | Morris et al. |
| 2010/0280449 A1* | 11/2010 | Alvarez ............ A61B 17/00234 604/95.04 |
| 2010/0286626 A1 | 11/2010 | Petersen et al. |
| 2010/0312096 A1 | 12/2010 | Guttman et al. |
| 2010/0312178 A1 | 12/2010 | Olsen et al. |
| 2011/0028826 A1 | 2/2011 | Kim et al. |
| 2011/0054465 A1 | 3/2011 | Werneth et al. |
| 2011/0060331 A1 | 3/2011 | Ibrahim et al. |
| 2011/0087112 A1 | 4/2011 | Leo et al. |
| 2011/0087175 A1 | 4/2011 | Krishnan et al. |
| 2011/0130750 A1 | 6/2011 | Ormsby et al. |
| 2011/0166455 A1 | 7/2011 | Cully et al. |
| 2011/0190784 A1 | 8/2011 | Hastings et al. |
| 2011/0213300 A1 | 9/2011 | McWeeney et al. |
| 2011/0224784 A1 | 9/2011 | Quinn |
| 2011/0245842 A1 | 10/2011 | Doan et al. |
| 2011/0251519 A1 | 10/2011 | Romoscanu |
| 2011/0264011 A1 | 10/2011 | Wu et al. |
| 2012/0010490 A1 | 1/2012 | Kauphusman et al. |
| 2012/0046666 A1 | 2/2012 | Klein |
| 2012/0071870 A1 | 3/2012 | Salahieh et al. |
| 2012/0109079 A1 | 5/2012 | Asleson et al. |
| 2012/0111482 A1 | 5/2012 | Grunewald et al. |
| 2012/0116199 A1 | 5/2012 | De La Rama et al. |
| 2012/0116200 A1 | 5/2012 | Roy et al. |
| 2012/0130217 A1 | 5/2012 | Kauphusman et al. |
| 2012/0130218 A1 | 5/2012 | Kauphusman et al. |
| 2012/0143099 A1 | 6/2012 | Daniels et al. |
| 2012/0143177 A1 | 6/2012 | Avitall |
| 2012/0203169 A1 | 8/2012 | Tegg |
| 2012/0232563 A1 | 9/2012 | Williams et al. |
| 2012/0239002 A1 | 9/2012 | Griswold |
| 2012/0277730 A1* | 11/2012 | Salahieh ............ A61B 1/00135 604/527 |
| 2013/0116705 A1 | 5/2013 | Salahieh et al. |
| 2014/0107623 A1 | 4/2014 | Salahieh et al. |

FOREIGN PATENT DOCUMENTS

| | | |
|---|---|---|
| EP | 1 525 897 | 4/2005 |
| WO | WO 2012/027383 | 3/2012 |
| WO | WO 2012/096816 | 7/2012 |

OTHER PUBLICATIONS

PCT/US2013/069470 International Search Report (Nov. 11, 2013).
The Extended European Search Report Application No. 13853310.4 dated Jul. 1, 2016.

* cited by examiner

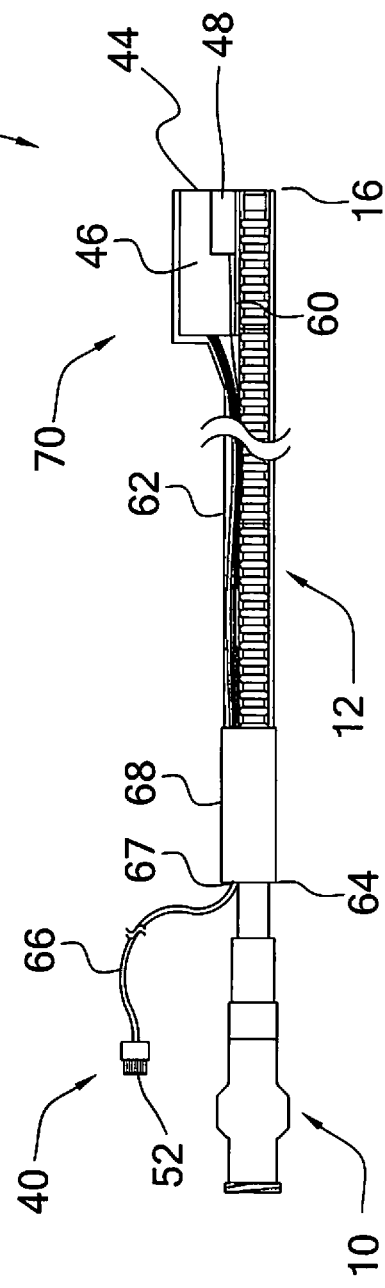
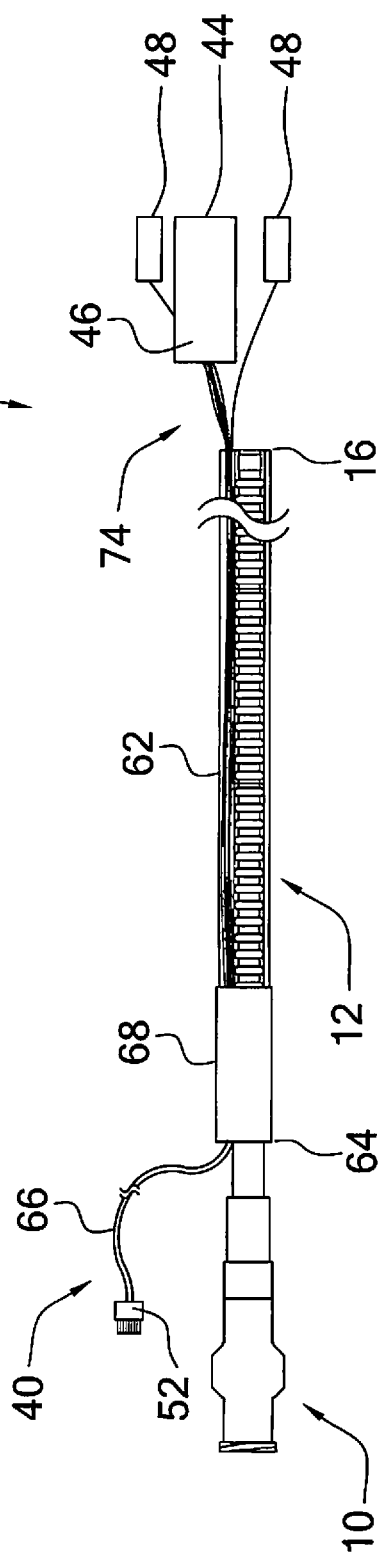
FIG. 3
FIG. 4

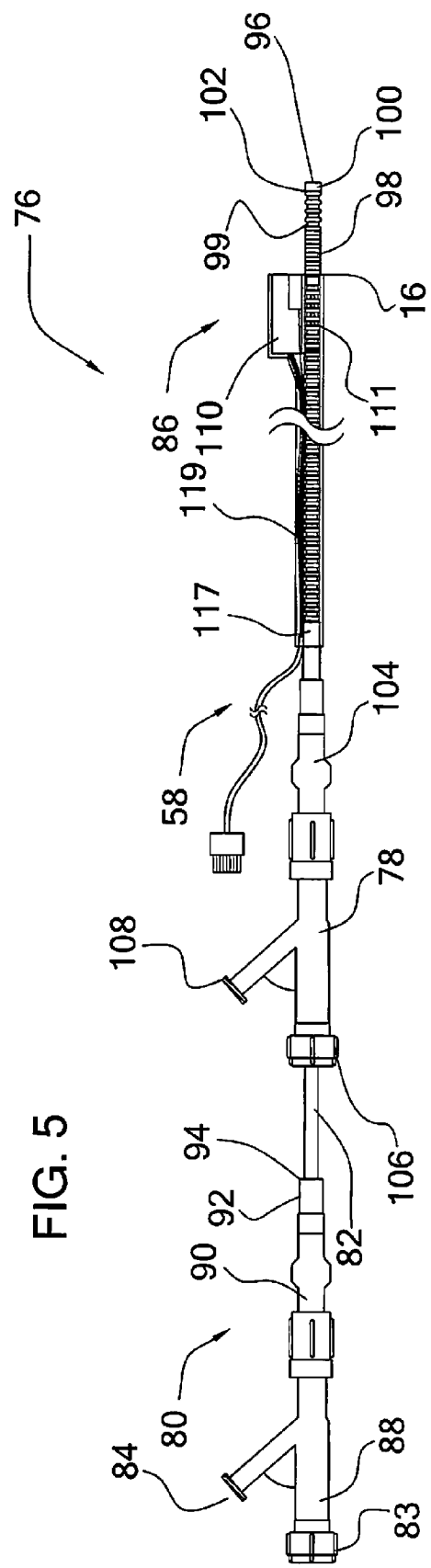

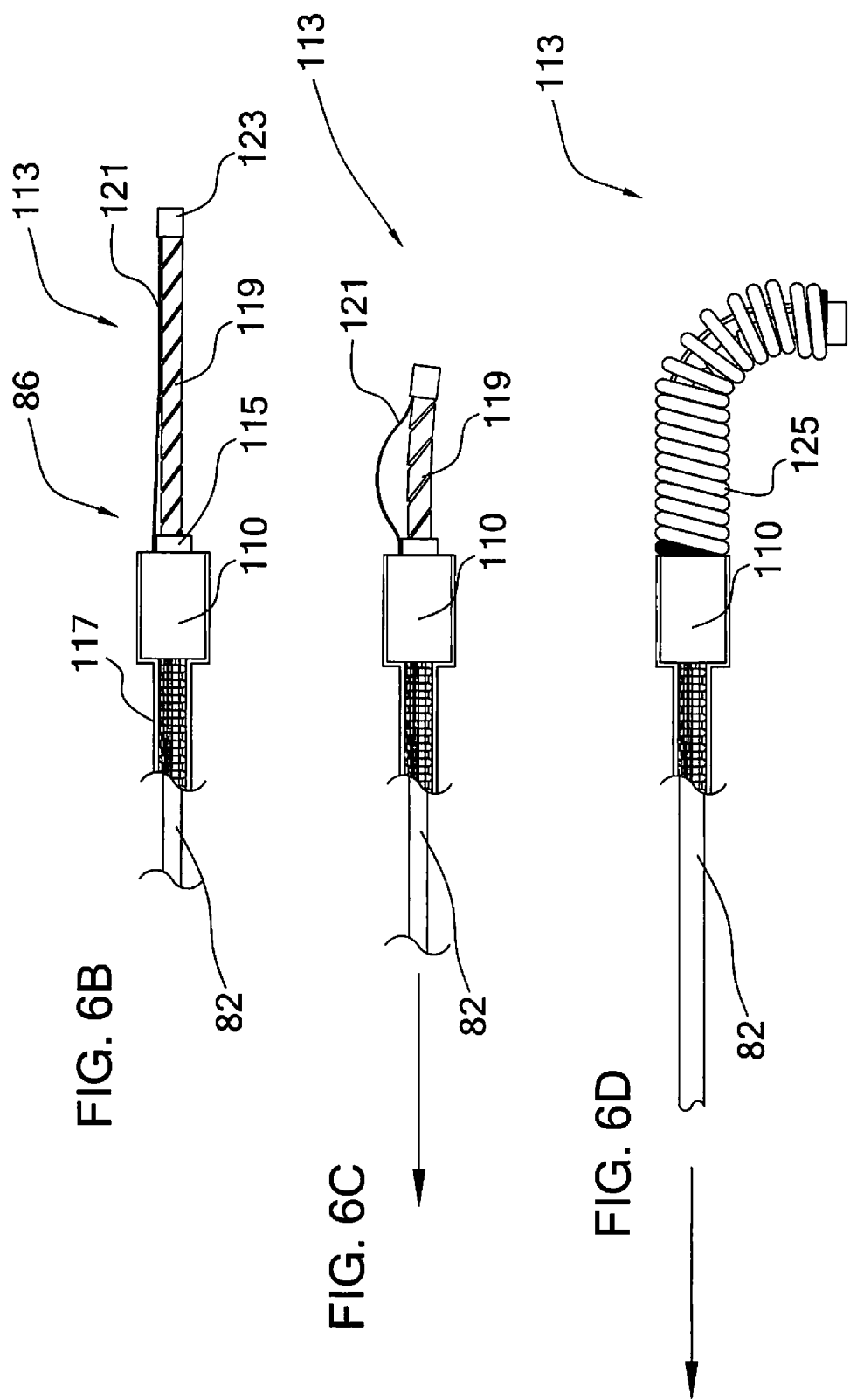

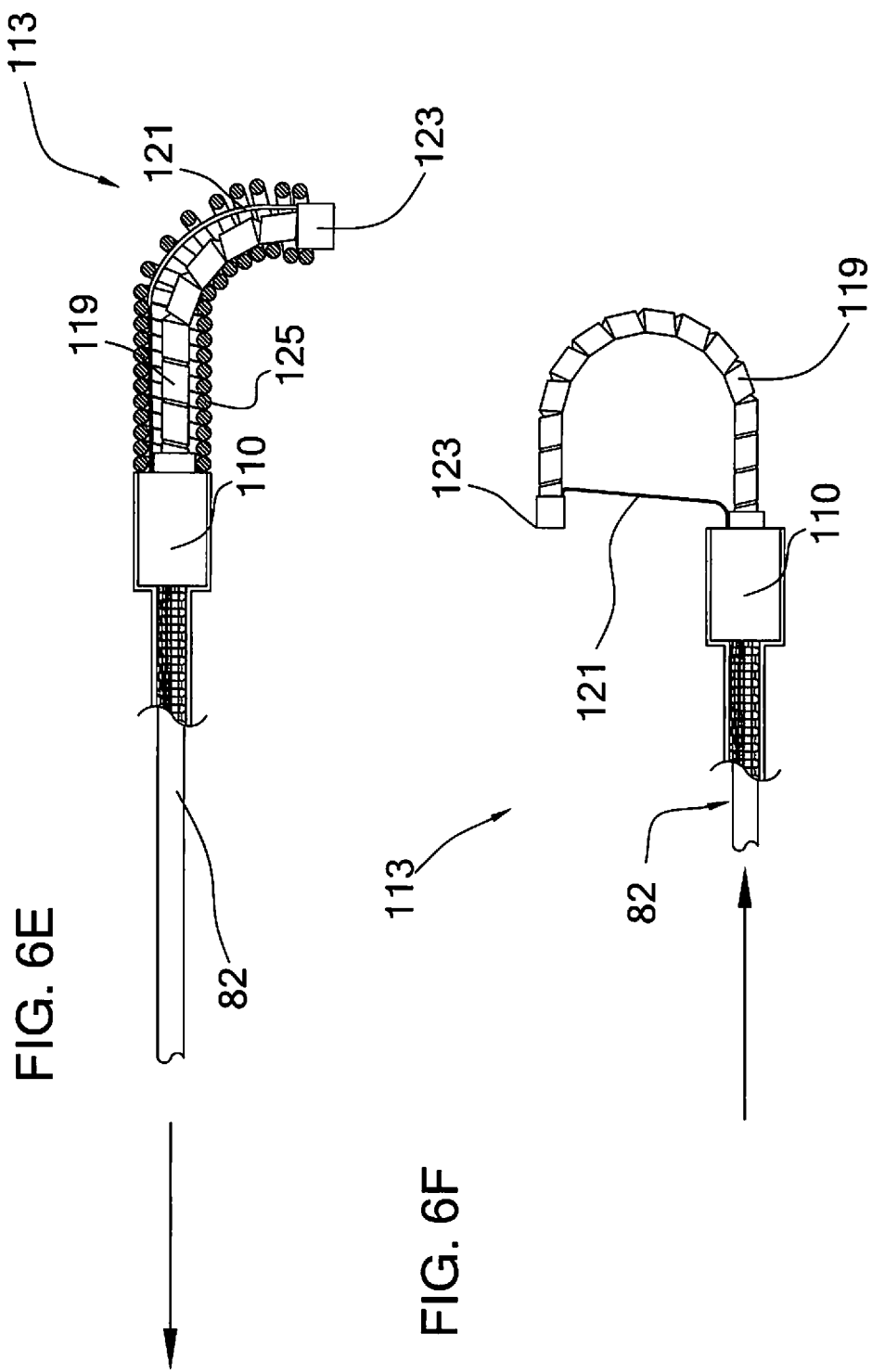

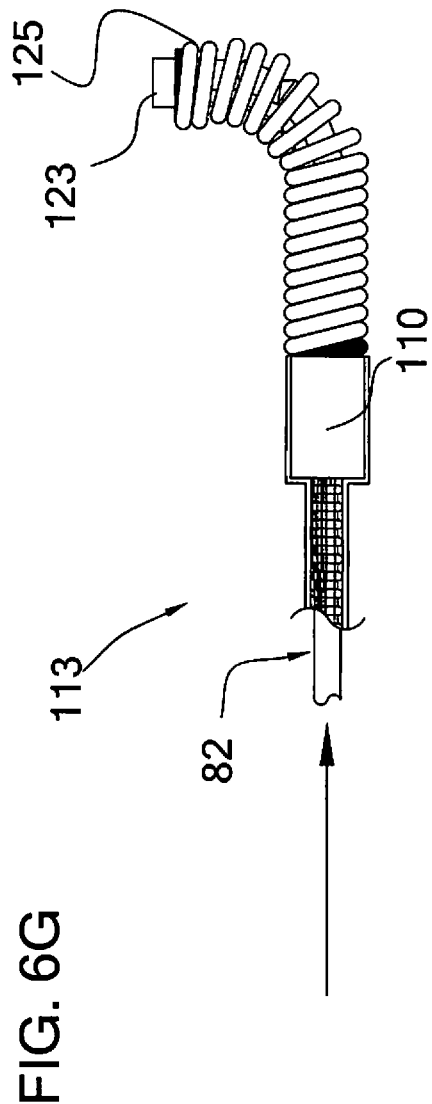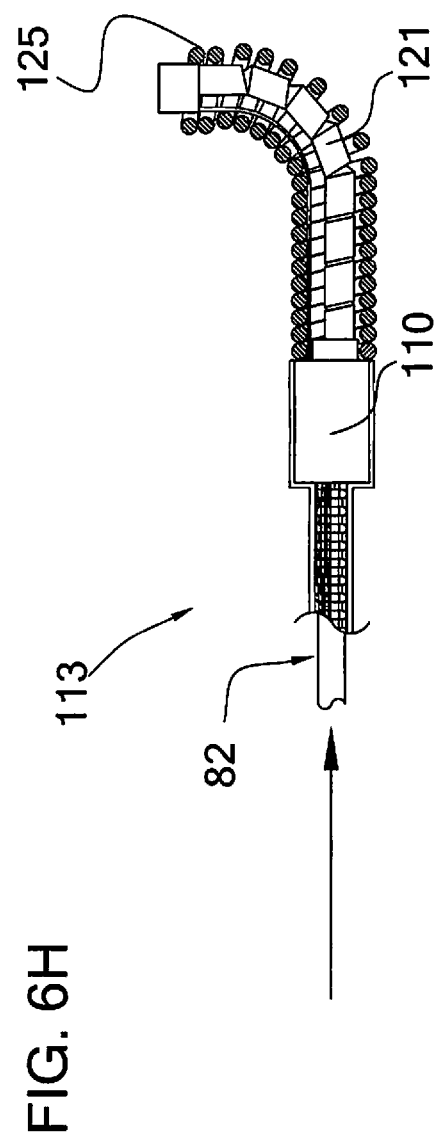

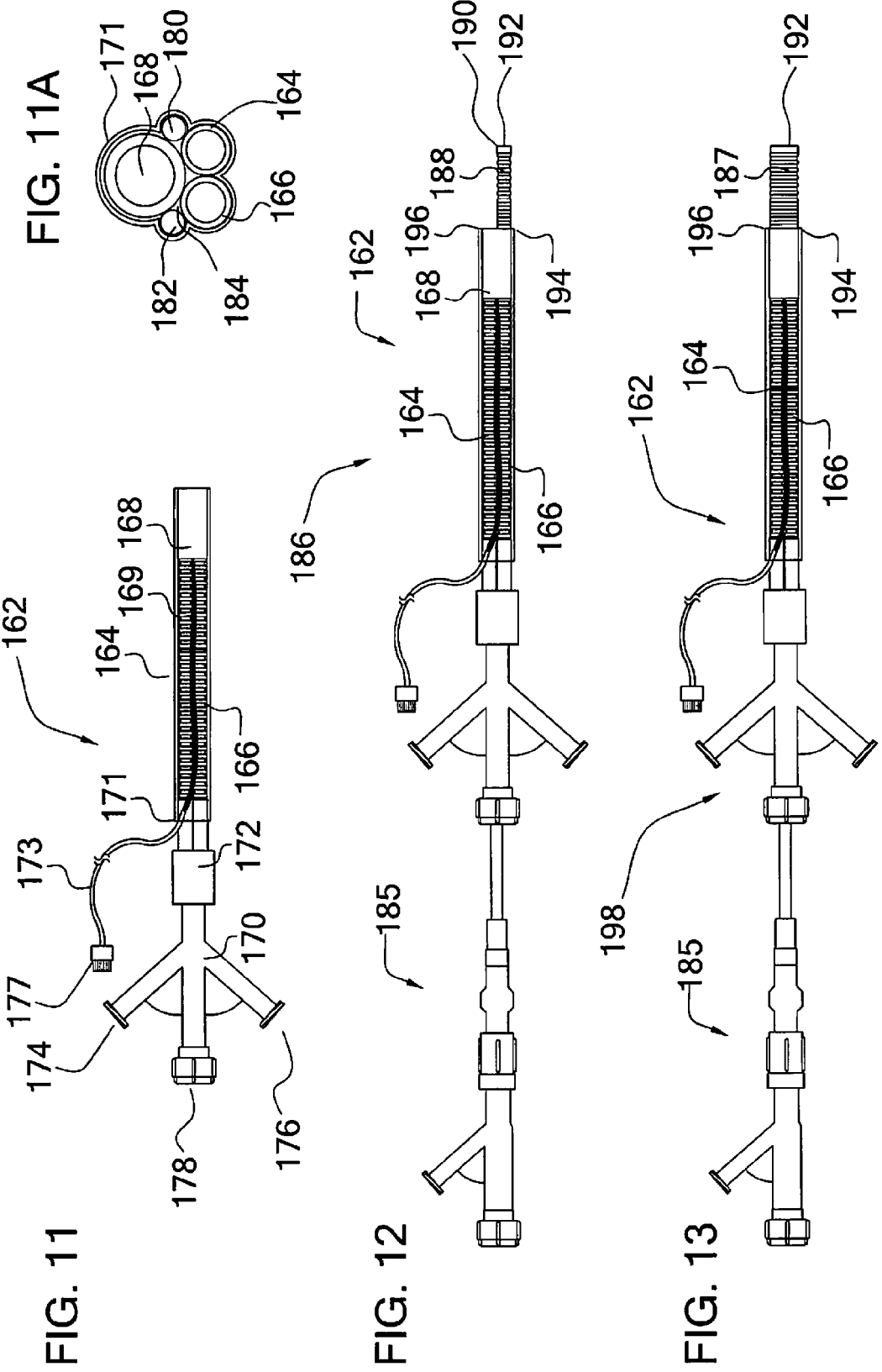

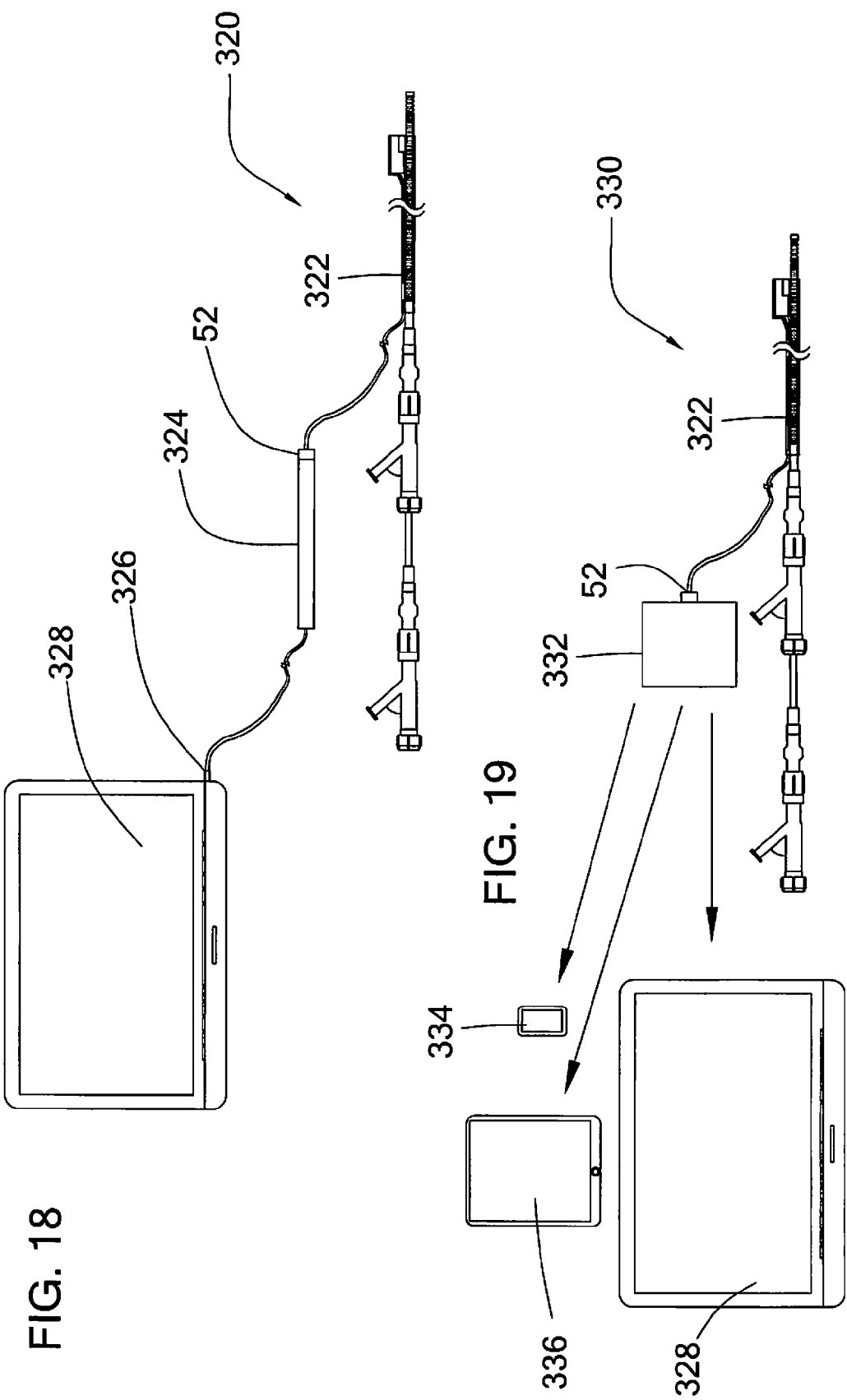

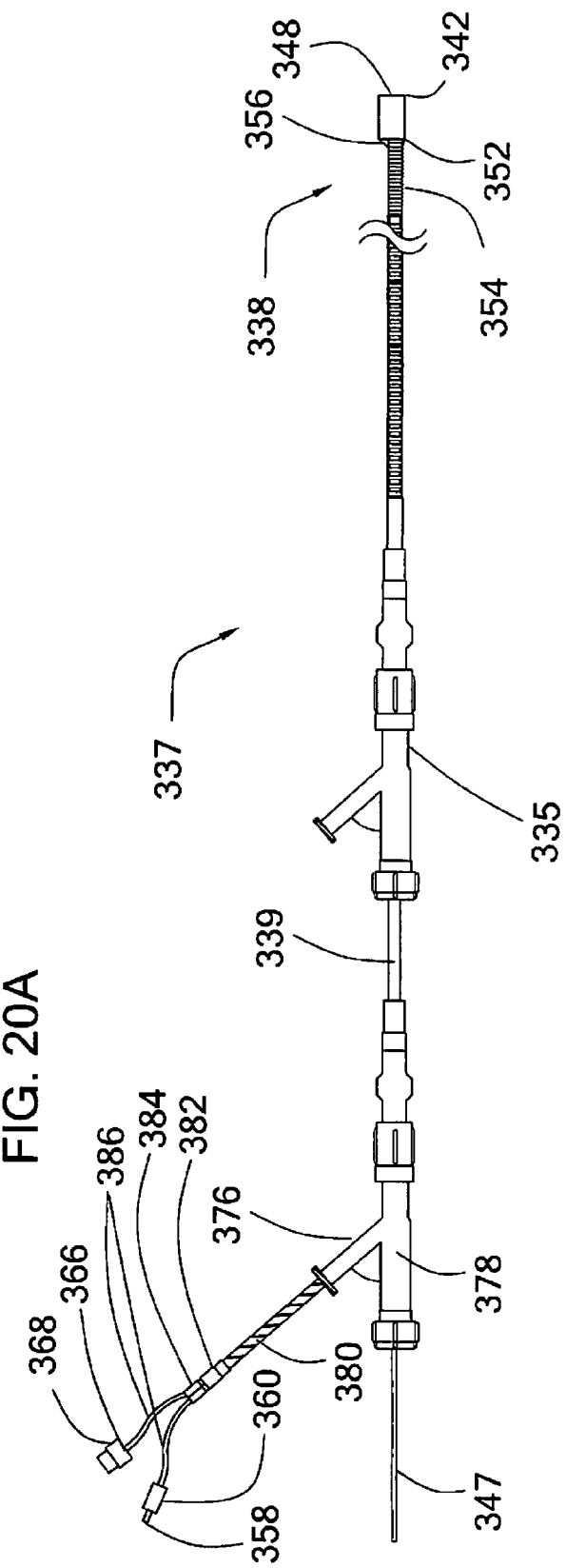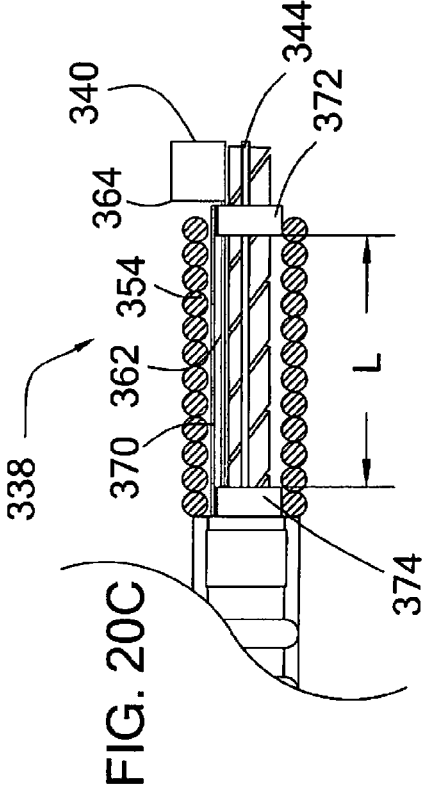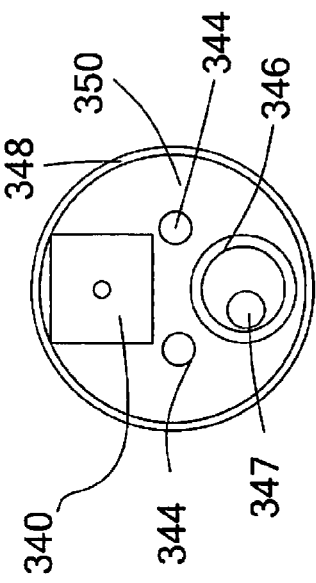

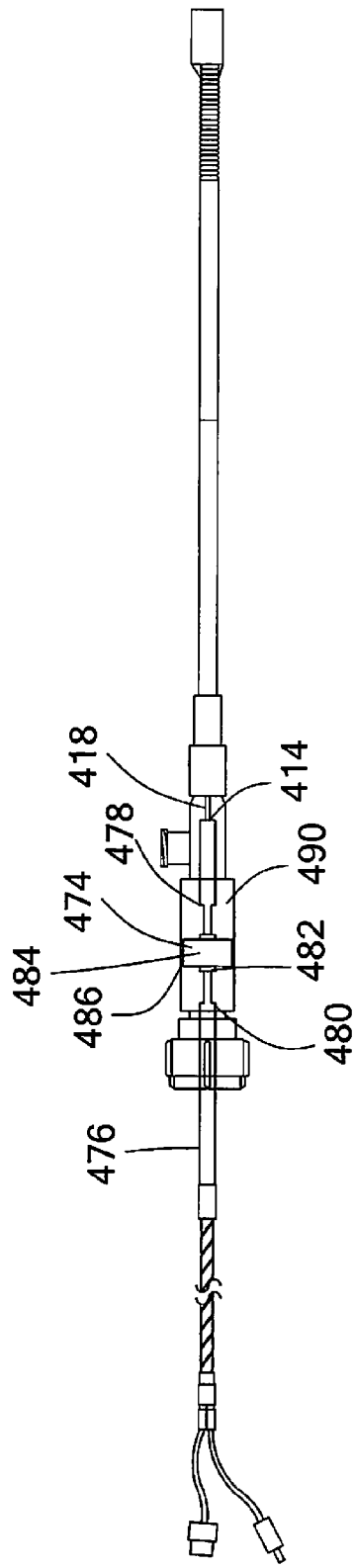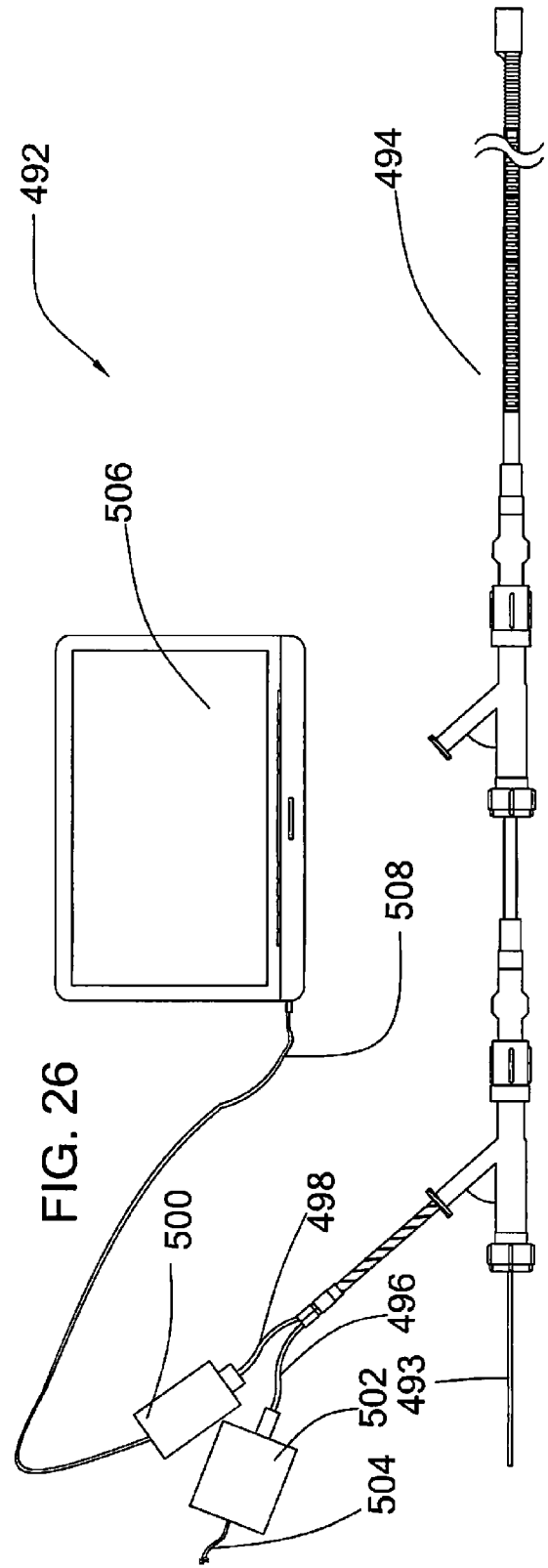
FIG. 25
FIG. 26

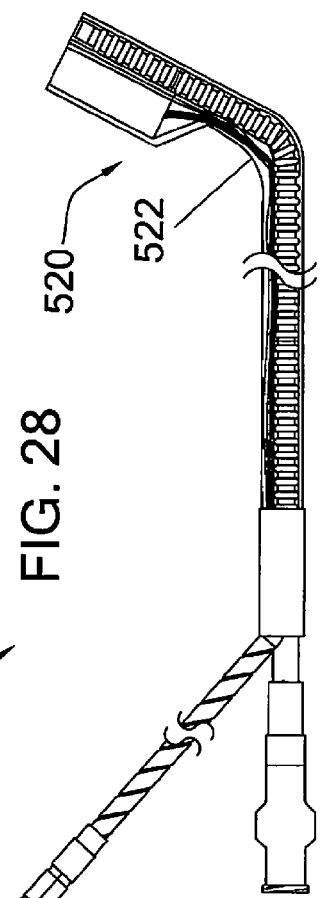
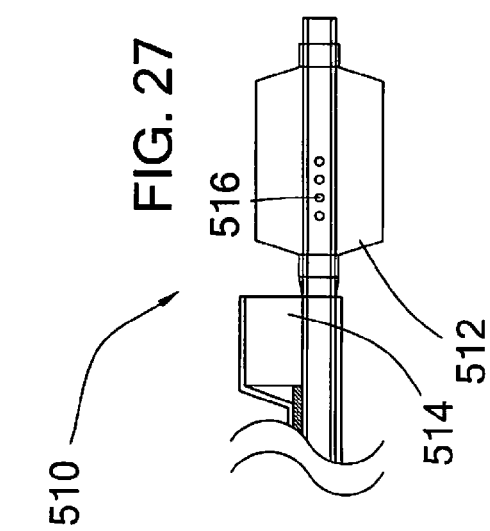

COAXIAL MICRO-ENDOSCOPE

This application claims priority from provisional application 61/724,922, filed Nov. 10, 2012, the entire contents of which are incorporated herein by reference.

BACKGROUND

Technical Field

The present invention generally relates to medical devices, and in particular medical catheters with optical capabilities and/or steering capabilities.

Background of Related Art

An endoscope is an illuminated usually fiber-optic flexible or rigid tubular instrument for providing direct visualization to the interior of a hollow organ or part (as the bladder or esophagus) for diagnostic or therapeutic purposes that typically has one or more channels to enable passage of instruments (as forceps or scissors). The scope is inserted through a natural opening, such as the mouth during a bronchoscopy or the rectum for a sigmoidoscopy.

Because current endoscopes have outer shaft diameters of approximately 5 mm or greater, they typically can only be used in relatively large body lumens. As a consequence, they can only provide direct visualization to the large lumen and the entrance to the small lumens that branch off. In order to examine a small lumen further, i.e., beyond the entrance, a catheter has to be inserted through the working channel of the endoscope and then passed down into the small lumen. Visualization is then done through radiographical means.

A variety of attempts have been made to provide catheters capable of navigating into small lumens to provide direct visualization and treatment. For example, U.S. Pat. No. 7,922,650 to McWeeney et al. discloses a direct visualization system that includes a reusable optical assembly and a disposable co-linear multi-lumen, steerable catheter that can be tracked over a guidewire. The catheter, which has a 10 French (3.3 mm) outer diameter, has one working channel, two irrigation channels, and a dedicated optical assembly lumen. The optical assembly, which has a diameter of approximately 0.77 mm is made of a fiber optic bundle surrounded by lights. Because the optical assembly is free of the catheter and has a small crossing profile it is able to enter normal bile and pancreatic ducts, which have diameters as small as 2 to 3 mm. However, the catheter itself, with a 3.3 mm crossing profile, is still restricted access. As a result, visualization which starts out moderate at best due to use of fiber optics is further impaired by any stone debris or sludge that cannot be properly flushed from a distance. In addition, the optical assembly is fragile and must be handled with care.

U.S. Pat. No. 7,922,654 to Boutillette et al. discloses a small diameter steerable imaging catheter with at least one steering cable extending along the catheter tube to control movement of the distal end and a fiber optic cable extending along the catheter tube. The catheter tube is constructed to have greater flexibility near its distal end portion while having greater stiffness in the remainder of the tube. It also discloses that this may be accomplished by varying durometer ratings of the materials used to form the catheter tube. It further discloses that this construction concentrates the flexing at the distal end portion, rather than throughout the entire catheter tube, to thereby reduce undue twisting of the catheter tube along its entire length, and further to permit better control of the movement of the distal end portion. In order to provide a smaller diameter steerable imaging catheter, the '654 patent provides a shaft with fewer independent channels (lumens) than the '650 patent which relies solely on shaft design and steering wires, not a guidewire, for navigation. The lack of independent channels results in the sharing of channels that are present. For instance, irrigation or flushing of the fiber optic may be interrupted if a cutting wire is needed for cutting out undesirable material. Interruption in flow will result in impaired visualization due to sludge or debris that cannot be properly flushed from in front of the fiber optic during the procedure. Also, the '654 patent uses fiber optic technology in the design due to its small delivery diameter. Like the '650 patent, this creates a fragile device with poor image quality.

Both of the above patents disclose co-linear multi-lumen tubes with at least one of the lumens dedicated to a fiber optic for viewing. In addition, both require the use of push/pull or steering wires, which are placed circumferentially around the catheter adding to the overall size.

There exists a need for smaller diameter devices with imaging capability. The need further exists for such smaller diameter devices that are highly navigable with an imaging technology that presents high resolution, color images to aid in the diagnosis and treatment of a patient. It would further be beneficial if such devices could be designed with deflection without increasing their size to thereby maintain their low profile. It would also be beneficial if such devices could enable flushing of the imaging devices to aid visualization.

SUMMARY OF INVENTION

The present invention overcomes the problems and deficiencies of the prior art.

The present invention provides in one aspect a deflectable endoscope comprising an imaging structure, an outer member having a proximal portion and a distal portion, an elongated column member extending distally from the outer member, and an inner member positioned coaxial with the outer member and attached to the column member. The inner member extends distally of the outer member and has a distal tip portion. A reinforcement member is positioned over the column member to restrict axial movement of the column member such that when one of the inner member or outer member is moved with respect to the other, axial compression of the column member is restricted by the reinforcement member causing the distal tip portion of the inner member to deflect laterally.

In some embodiments, the outer member has a central longitudinal axis and the column member is radially offset with respect to the central longitudinal axis of the outer member.

In some embodiments, the lateral reinforcement member comprises a tube. In some embodiments, the tube is a helically wound flexible coil. In some embodiments, the column member is fixedly attached to the outer member and the inner member. In other embodiments, the column member is attached only to the inner member.

The outer member can have a central lumen to receive the inner member and/or the inner member can have a central lumen to receive a guidewire or other accessory. The central lumen of outer member can be lubricated to facilitate movement of the inner member therein to facilitate deflection.

The column member is preferably non-circular in cross section. In some embodiments, the column member has a proximal portion attached to the distal portion of the outer member and a distal portion attached to the distal portion of the inner member.

The endoscope can further include a marker band at the distal portion of the inner member and the column can be attached to the marker band. In some embodiments, a proximal portion of the column member terminates at a distal portion of the outer member.

Preferably, upon movement of the inner member proximally or the outer member distally, the axial compression of the column member is limited by the reinforcement member so it cannot fail axially but instead fails laterally to deflect the distal tip portion.

In some embodiments the endoscope includes first and second marker bands on the inner member, and the column member is attached to the first and second marker bands.

A locking assembly can be provided to lock the position of the inner member with respect to the outer member.

The inner member can have a cut tube at its distal end portion to provide flexibility.

In some embodiments, the imaging structure is attached to the outer member and does not deflect with the distal tip portion. In other embodiments, the imaging structure is attached to the inner member and deflects with the distal tip portion. In some embodiments, the imaging structure includes a complementary metal-oxide-semiconductor module. A lighting structure can be integrated with the imaging structure or alternatively a separate component from the imaging structure.

In accordance with another aspect of the present invention, a deflectable endoscope is provided comprising a proximal portion, an intermediate portion, a deflectable distal tip portion and an imaging device. A first movable member is axially movable from a first position to a second position, wherein the distal tip portion is deflectable by an axial movement of the first member in which the distal tip portion cannot fail axially in compression so it fails laterally causing deflection of the distal tip portion in a first direction.

In some embodiments, the first movable member is positioned within a second member, and the first position is distal of the second position. In other embodiments, the first movable member is positioned over a second movable member and the first position is proximal of the second position. In some embodiments, the first movable member deflects while the second movable member remains substantially stationary or substantially non-deflected. In some embodiments, axial movement in an opposite direction causes a bending of the distal tip portion in the opposite direction.

In some embodiments the imaging device is attached to the outer member and does not deflect with the distal tip portion. In some embodiments, the imaging device is attached to the inner member and deflects with the distal tip portion.

The present invention provides in accordance with another aspect a deflectable endoscope having a deflectable distal tip portion comprising an outer catheter having a lumen, a proximal portion and a distal portion, an elongated member extending distally from the outer member, and an inner catheter positioned coaxially within the inner lumen of the outer catheter and attached to the elongated member, wherein axial movement of one of the outer member and inner member causes the distal tip portion of the catheter to deflect laterally. An imaging device is carried by one or both of the inner or outer catheters.

In some embodiments, the elongated member is attached to the inner member and is surrounded by a movement restriction member to restrict axial movement of the column member when the outer member or inner member is moved axially relative to the other. Preferably, such axial restriction limits axial compression of the column member upon axial movement in one direction. In some embodiments, a tip of the inner catheter deflects and a tip of the outer catheter remains substantially non-deflected.

Preferably, movement of the inner catheter in one direction causes axial compression of the elongated member and movement of the inner catheter in a second direction causes bending of the elongated member to cause deflection in a second opposite direction.

In accordance with another aspect of the present invention, a deflectable endoscope is provided having a deflectable distal tip portion. The endoscope includes an imaging device, an outer catheter having a lumen, a proximal portion and a distal portion, an inner catheter positioned coaxially within the inner lumen of the outer catheter and having a distal tip portion extending distally of a distal end of the outer catheter, and a column member attached to the inner catheter, wherein axial movement of one of the outer member and inner member acts on the column member to cause the distal tip portion of the inner catheter to deflect laterally.

In some embodiments, the column member includes a proximal stop contacted by the outer catheter.

In accordance with another aspect of the present invention, a micro-endoscope is provided having an outer member having a proximal portion, a distal portion, an outer surface and an inner surface, and an imaging device positioned on an outer surface of the outer member and including transmission members extending proximally to the proximal portion of the outer member. In some embodiments, the transmission members extend through a lumen in the outer member. In other embodiments, the transmission members extend along the outer surface of the outer member. In some embodiments the imaging device is mounted at a distal tip of the outer member. In some embodiments the imaging device includes a complementary metal oxide semi-conductor module. In some embodiments, a tubing is positioned over the imaging device and over a least a portion of the outer surface of the outer member to retain the imaging device on the outer surface.

The present invention also provides in accordance with another aspect a deflectable coaxial catheter comprising an inner catheter, an outer catheter positioned coaxially over the inner catheter wherein relative movement of the inner and outer catheters deflects a distal tip portion of the coaxial catheter, and an imaging structure carried by one or both of the inner catheter and outer catheter. In some embodiments, the imaging structure is proximal of the deflecting distal tip portion. In other embodiments, the imaging structure is attached to the deflecting distal tip portion.

In some embodiments, the imaging structure is mounted on an outer surface of the outer catheter. In other embodiments, the imaging structure is attached to an outer surface of the inner member.

The catheter can further comprise a tubing positioned over the imaging structure to secure the imaging structure to the other surface of the catheter.

In accordance with another aspect of the present invention, a deflectable endoscope is provided comprising a proximal portion, an intermediate portion, a deflectable distal tip portion and an imaging device. The imaging device is axially movable from a first position to a second position, wherein the distal tip portion is deflectable by an axial movement of the imaging device in which the distal tip portion cannot fail axially in compression so it fails laterally causing deflection of the distal tip portion in a first direction. In some embodiments, the imaging device includes as optical fiber. In some embodiments, the imaging device is positioned within an outer member. In some embodiments, the imaging device includes a data cable.

The present invention also provides in accordance with another aspect a coaxial bi-directional deflectable microendoscope which can be lubricated internally through external application to help overcome friction between the inner catheter and the outer catheter while deflecting the distal tip in narrow, tortuous vasculature. In a method for lubricating the deflection lumen formed by the inner diameter of the outer catheter, a syringe filled with fluid can be connected to a side arm. The side arm can be part of a locking assembly, and prior to the procedure, with the locking assembly in a locked position, fluid can be injected into the inner lumen of the outer catheter. The locking assembly can then be opened and the inner catheter pulled and pushed to deflect the tip, with the fluid ensuring smooth movement. With the locking assembly locked, the catheter and guidewire can then be inserted and tracked through the anatomy. If, at any point, deflection is impaired, additional lubrication fluid can be introduced through the side arm using a syringe.

The present invention also provides a coaxial micro-endoscope which overcomes current limitations in diameter, image quality and navigation. The present invention provides in some aspects a coaxial microcatheter with video visualization technology held in close contact with the outer diameter of the catheter. In deflectable micro-endoscope embodiments, it uses the inner catheter to bring about bi-directional deflection. It also can provide irrigation introduced between the catheters to facilitate relative movement and thus deflection.

The small diameter coaxial micro-endoscope and the small diameter coaxial bi-directional (deflectable) micro-endoscope of the present invention can be used as a stand-alone scope or inserted into a larger endoscope as part of a procedure such as examination of biliary or pancreatic ducts. The micro-endoscope is designed to navigate using a guidewire in combination with a deflectable tip. In addition, video technology is piggybacked on the micro-endoscope's outer catheter where it is held in place such as by a highly flexible tube thereby reducing the need for a dedicated imaging lumen.

Various methods for attaching an imaging or treatment technology to the outer wall of a medical device are provided.

In accordance with one aspect of this invention, a non-deflectable micro-endoscope is provided, including a microcatheter, a complementary metal-oxide-semiconductor (CMOS) module (consisting of a lens, CMOS sensor, and flexible printed circuit (FPC) glued inside a protective housing), lighting, miniature coaxial cables connecting the CMOS module and lighting to a proximal connector, and a polymer heat shrink tube. In an exemplary construction, the CMOS module and lighting are adhered to the distal end of the microcatheter and a portion of the miniature coaxial cables connected to them is stretched along the exterior of the microcatheter's substantially useable length towards the catheter's proximal end. Attachment external to the micro-endoscope reduces the overall diameter of the micro-endoscope since it does not need internal space to accommodate the imaging and lighting system. Polymer heat shrink tubing can cover the microcatheter, CMOS module/lighting and coaxial cables along a portion of the useable length of the microcatheter. The polymer heat shrink tube serves to keep the miniature coaxial cables in close contact with the microcatheter body as well as an outer jacket for the entire assembly. A Rotating Hemostatic Valve (RHV) can be attached to the winged hub (luer) at the proximalmost end of the microcatheter to allow inner lumen access as well as irrigation and/or insufflation at the distal end. The inner lumen of the microcatheter can serve as the working channel of the micro-endoscope for passage of guidewires, biopsy forceps, RF cutting wires, fiber optics, or other accessories needed for carrying out diagnostic or therapeutic functions. The micro-endoscope's microcatheter body can be designed with a variable stiffness shaft for tracking over a guidewire. Hydrophilic coating may be introduced to the outer jacket to help with movement. The portion of the coaxial cables that are free (not in contact with the catheter body) can also be in a protective jacket made of either an extrusion or protective shrink tubing. An optional strain relief can be placed over the proximal end of the catheter where the distal end of the free miniature coaxial cables covered in extrusion or protective shrink tubing meet the proximal end of the outer catheter and miniature coaxial cables covered in the polymer heat shrink tube. Preferably, at the very proximal end of the free miniature coaxial cables is a connector. The connector can be used to connect to an interface board, which mates the micro-endoscope with devices such as a video processing/display system, computer, tablet (IPad), or smart phone for viewing and/or recording. The entire micro-endoscope including connector can be disposable or, if desired, re-usable with proper cleaning.

In accordance with another aspect of the present invention, a coaxial bi-directional (deflectable) micro-endoscope is provided including a coaxial bi-directional microcatheter and an imaging system held in close contact to the outer catheter with a shrinkable polymer cover. In the preferred construction, the micro-endoscope described in the previous embodiment will serve as the outer catheter for the coaxial bi-directional micro-endoscope described here. An inner catheter, with a length greater than the useable length of the outer catheter, is slidably disposed through the outer catheter which is provided with an imaging system and RHV. The distal end of the inner catheter, which extends past the distal end of the outer catheter, is configured for deflection and covered with a flexible helical coil. The proximal end of the inner catheter can have an RHV. The inner lumen of the inner catheter of the coaxial bi-directional micro-endoscope can serve as the working channel for passage of guidewires, forceps, optical biopsy devices or other accessories needed for carrying out diagnostic or therapeutic functions. Air/gas irrigation and/or insufflation can in some embodiments be introduced through a side arm of the RHV on the proximal end of the outer catheter and can exit the distal end of the outer catheter through holes in the outer shaft or through gaps or holes formed on the deflectable distal tip. In some embodiments, additional irrigation and/or insufflation can be introduced through the side arm on the RHV on the proximal end of the inner catheter. The inner lumen of the inner catheter also serves to deflect the distal tip. To do this, in some embodiments, the lock (end cap on the RHV) on the proximal end of the outer catheter is opened, freeing the inner catheter to move axially back and forth causing the distal tip to deflect. Deflection occurs as the inner catheter is pulled proximally (or the outer catheter is moved distally), thereby compressing the column at the distal end. When the inner catheter is pushed distally (or the outer catheter is moved proximally), the column will bend causing the distal tip to deflect in the opposite direction. The coaxial bi-directional micro-endoscope can have in some embodiments variable stiffness shafts designed to be pushed and tracked over a guidewire. Hydrophilic coating may be introduced on both the inner catheter and outer catheter to help with movement.

In accordance with another aspect of the present invention, a coaxial bi-directional micro-endoscope is provided including a coaxial bi-directional microcatheter with imaging and lighting positioned on the deflecting distal tip portion of the micro-endoscope. In some embodiments, the CMOS module and lighting with a portion of the coaxial cables extend past the distal end of the outer catheter of the coaxial bi-directional microcatheter. The CMOS module and lighting can be attached to the distal end of the deflectable tip portion of the micro-endoscope. The attachment orientation can in some embodiments be parallel and in other embodiments perpendicular to deflection. In some embodiments, the miniature coaxial cables running along the exterior of the outer catheter of the coaxial micro-endoscope can be held in contact by the polymer shrink tubing, while the distal deflecting tip portion with CMOS module and lighting can be covered with a more flexible tube such as balloon tubing.

In accordance with another aspect of the present invention, a coaxial bi-directional micro-endoscope is provided including a dual lumen coaxial bi-directional microcatheter with an imaging and lighting system. In the preferred construction, a second outer catheter is placed parallel to the outer catheter for the coaxial bi-directional microcatheter. The CMOS module and lighting are then adhered to a distal end of the outer catheter and a polymer cover can be shrunk around all three parts to create the dual lumen outer catheter. The inner catheter and remaining parts can then be added to complete the coaxial bi-directional micro-endoscope. If desired, the distal deflection coil can cover one or both outer catheters.

In some embodiments, the protective distal housing for the CMOS module can be replaced with an adhesive barrier that tapers from distal to proximal.

In accordance with another aspect of the present invention, a non-deflectable coaxial micro-endoscope with a removable inner catheter is provided. In the preferred construction, the inner catheter is slidably disposed through the outer catheter so that their distal ends are flush. As in previous aspects, the CMOS module, lighting, and miniature coaxial cables can be kept in close contact with the outer catheter with a polymer shrink tubing or by other methods. The lumen formed between the inner catheter and the outer catheter can be used for irrigation and/or insufflation, which is introduced through an RHV on the proximal end of the outer catheter. Accessories can be delivered through the inner lumen of the inner catheter. Should a larger working channel be needed, the inner catheter can be removed so that the inner lumen of the outer catheter becomes the working channel for the micro-endoscope.

In accordance with another aspect of the present invention, a coaxial bi-directional micro-endoscope with no working channel is disclosed. In one construction, the miniature coaxial cables can run through the inner lumen of the inner catheter of the coaxial bi-directional micro-endoscope and the CMOS module and lighting are connected to the distal end of the micro-endoscope. Irrigation and/or insufflation can be introduced through the side arm on the RHV at the proximal end of the outer catheter. Exit holes for irrigation/insufflation can be cut into the outer shaft or gaps can be introduced in the deflectable tip coil.

In accordance with another aspect of the present invention, a method for the attachment of an imaging, treatment, or lighting system to a catheter is provided. In one construction, the distal end of the imaging, lighting, or treatment system is adhered to the distal end of the medical device and then the fibers or cables are stretched to the desired length along the exterior of the device and a heat shrink tubing is slid over the assembly. Heat is applied to shrink the tubing down so that the fibers or cables come in close contact with the exterior of the device where they are held in position. The remaining free cables can be encapsulated in another shrink tubing or may come from the factory covered with a protective extrusion. An optional strain relief can be placed over the distal end of cables covered by the shrink tubing or extrusion where it meets the proximal end of the shrink tubing covering the device/miniature coaxial cables. If the medical device is a balloon catheter, the image, lighting, or treatment system can be placed on the main catheter body (proximal of the balloon), on the distal tip (distal of the balloon), on a point in between.

The micro-endoscope of the present invention provides in-vivo visualization systems that are suitable for viewing and/or performing diagnostic and therapeutic modalities in the human body, such as in the biliary tree.

BRIEF DESCRIPTION OF THE DRAWINGS

FIG. 3 illustrates the microcatheter of FIG. 1 with the CMOS module structure of FIG. 2 attached externally using polymer shrink tubing in accordance with one embodiment of the present invention;

FIG. 4 is a side view of an alternate embodiment of a microcatheter with CMOS module structure with the distal-most CMOS housing and lighting free of shrink tubing and mountable to an inner catheter (not shown);

FIG. 5 illustrates a deflectable coaxial bi-directional micro-endoscope in accordance with one embodiment of the present invention which includes the outer catheter of FIG. 3 and a first embodiment of an inner catheter;

FIG. 6A is an enlarged top view of the distal portion of the coaxial bi-directional micro-endoscope of FIG. 5 showing tip deflection relative to CMOS module placement;

FIG. 6B is a side view of the deflection structure of the micro-endoscope shown in the non-deflected position and shown with the lateral reinforcement (support) tube removed for clarity;

FIG. 6C is a side view similar to FIG. 6B showing deflection of the distal tip upon retraction of the inner catheter in the absence of the lateral (axial) reinforcement (support) tube;

FIG. 6D is a side view showing deflection of the distal tip in the presence of the lateral reinforcement tube;

FIG. 6E is a view similar to FIG. 6D showing a portion of the reinforcement tube cut away to show movement of the column;

FIG. 6F is a side view showing deflection of the distal tip upon advancement of the inner catheter in the absence of the lateral reinforcement tube;

FIG. 6G is a side view showing deflection of the distal tip when the inner catheter is advanced in the presence of the lateral reinforcement tube;

FIG. 6H is a view similar to FIG. 6G showing a portion of the reinforcement tube cut away to show movement of the column;

FIG. 11 is a side view of an alternate embodiment of an outer catheter for the coaxial bi-directional micro-endoscope with CMOS module, the outer catheter being a dual lumen catheter and the CMOS structure attached with polymer tubing;

FIG. 11A is an enlarged front view of the dual lumen outer catheter of FIG. 11;

FIG. 12 illustrates a coaxial bi-directional micro-endoscope in accordance with one embodiment of the present invention including the dual lumen outer catheter of FIG. 11 and the inner catheter of FIG. 5 with a single deflecting lumen;

FIG. 13 illustrates a coaxial bi-directional micro-endoscope in accordance with yet another embodiment including the dual lumen catheter of FIG. 11 and another embodiment of the inner catheter for dual lumen deflection as the coil covers both lumens;

FIG. 18 illustrates one embodiment of a coaxial bi-directional micro-endoscope visualization system;

FIG. 19 illustrates another embodiment of a coaxial bi-directional micro-endoscope visualization system using a wireless router;

FIG. 20A is a side view of another embodiment of the coaxial bi-directional micro-endoscope of the present invention;

FIG. 20B is a front view of the micro-endoscope of FIG. 20A;

FIG. 20C is an enlarged view in partial cross section of the distal portion of the micro-endoscope of FIG. 20A.

FIG. 25 side view of another embodiment of the coaxial bi-directional micro-endoscope of the present invention;

FIG. 26 is a side view of another embodiment of the coaxial bi-directional micro-endoscope of the present invention shown with a visualization system;

FIG. 27 is a side view of a distal portion of an alternate embodiment of the micro-endoscope of the present invention having a balloon; and FIG. 28 is a side view of another embodiment of the coaxial bi-directional micro-endoscope of the present invention having a preformed distal portion.

DETAILED DESCRIPTION

Figure 1:
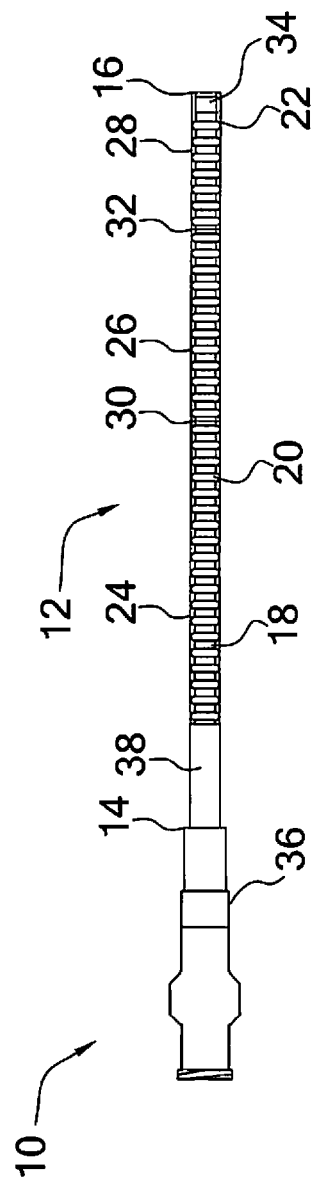
FIG. 1 is a side view of one embodiment of a variable stiffness microcatheter.

FIG. 1 illustrates a first embodiment of a microcatheter 10. The microcatheter can be used with the non-deflectable or the deflectable (bi-directional) systems disclosed herein. The microcatheter is used with the imaging systems described herein to form the endoscope or micro-endoscope (visualization device) of the present invention. The microcatheter can also be used with the inner catheters described herein to form the deflecting micro-endoscope of the present invention. Each of these systems is discussed below.

The microcatheter 10 includes a catheter body 12 that runs from proximal end 14 to distal end 16. Catheter body 12 has a lubricious inner liner 18 that runs from proximal end 14 to distal end 16. The purpose of the liner is to help reduce the coefficient of friction to aid in guidewire movement within the lumen of the catheter body 12. The liner can be made of materials such as polytetrafluoroethylene (PTFE) or fluorinated ethylene propylene (FEP). Other materials are also contemplated.

The liner is topped with an open pitch continuous coil 20 to help with lumen integrity (reinforcement) and to aid in stiffness variation. The coil 20, which can be made of flat or round wire or a combination, runs from proximal end 14 to distal end 22. The coil can be made of materials such as stainless steel, nitinol, polymer, platinum/iridium, fiber or even a combination of materials. In addition, it can be open or closed pitch or a combination of the two. The coil can also be replaced in part or in whole by a braid.

The coil reinforcement layer is then topped with polymers with varying stiffnesses to create three distinct sections: proximal section 24, mid section 26, and distal section 28. Proximal section 24 extends distally from proximal end 14 to distal end 30. Mid section 26 extends distally from distal end 30 of proximal section 24 to distal end 32. Distal section 28 extends from distal end 32 of the mid section 26 to distal end 16. The stiffness will decrease from proximal section 24 to distal section 28. Reduction in stiffness can be achieved by using decreasing durometers of material from proximal to distal. Preferably, proximal section 24 can be formed using materials such as nylon or pebax having a durometer in the range of 60D to 75D or any other material having a relative durometer hardness value of about 72D, mid section 26 can be formed using a lower hardness material with a durometer of about 63D, and distal section 28 can be formed with an even lower hardness material such as a pellethane material having a durometer of 25D to 55D or other material having a durometer between about 25D and about 40D. These are just examples of materials and durometers that can be used as other materials and durometers are also contemplated. Also, each section does not need to be formed with a single layer of material, if desired, sections can be constructed of two or more layers. Actual material selection will be based on design needs for flexibility and stiffness. Additional layers of coils or braids may also be added as needed. If needed, marker band 34 may be placed near the distal end 16. The marker band can be made of platinum/iridium to aid in visualization under fluoroscopy or of other metals or plastics. The band can also be made from a coil rather than a solid tube as shown or even left off the design. These layers are then fused together using a re-flow process (heat). Coupled to the proximal end of outer catheter body 12 is winged hub (luer) 36, which sits on optional strain relief 38. The winged hub (luer) 36 can be made of plastic.

As stated above, the typical microcatheter is formed using a re-flow technique which fuses all of the layers together with heat and, if necessary, removable heat shrink tubing. As the length, which can range from about 0.5 inches to about 34 feet, increases to greater than about 180 cm the use of the re-flow technique may be a problem due to current equipment restrictions. An alternate method is to use non-removable heat shrink tubing of varying stiffnesses to create the proximal, mid, and distal sections. Also, FIG. 1 shows one construction for a variable stiffness microcatheter. Other combinations or variations are considered to be within the scope of this disclosure. If desired, the catheter need not have any stiffness variation at all, it can be constructed of a single durometer tube, an extrusion of single or multiple lumens, polyimide or metal (with or without laser cutting for flexibility). The design concept described in FIG. 1 or something similar can be used for constructing both the inner and outer catheters for the coaxial bi-directional micro-endoscope discussed below.

Figure 2:
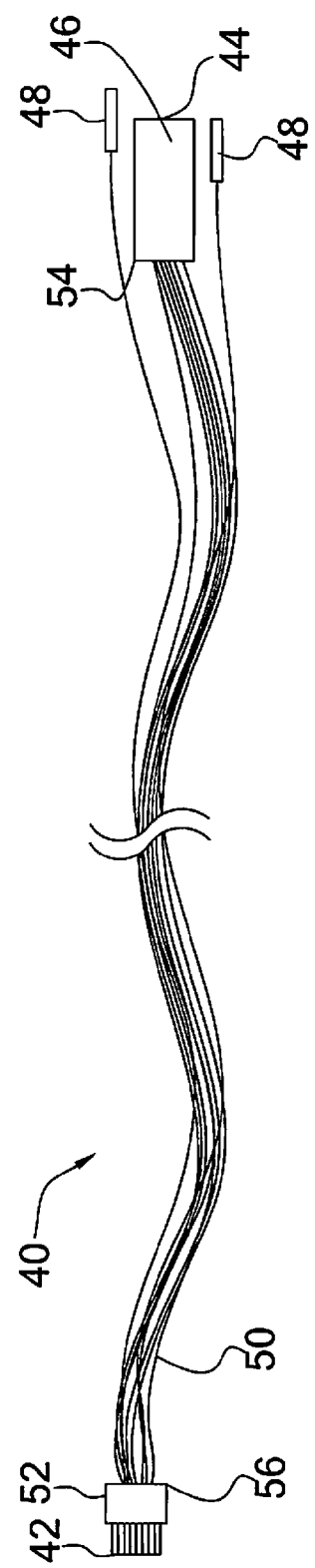
FIG. 2 illustrates a CMOS module structure having a CMOS module housing and lighting connected to a proximal connector by miniature coaxial cables.

FIG. 2 illustrates a complementary metal-oxide-semiconductor (CMOS) imaging device or structure 40 such as those built by Fujikura (Japan) or Medigus (Israel). The structure 40 extends from proximal end 42 to distal end 44 and includes a CMOS module 46, lighting 48, miniature coaxial cables 50, and a connector 52. The CMOS module 46 is at the distal end of imaging structure 40. The module 46 has a housing that extends from proximal end 54 to distal end 44. The CMOS module houses (not shown) a lens, a CMOS sensor, and a flexible printed circuit (FPC), which are connected to the miniature coaxial transmission cables 50, all of which are glued together inside the housing. The CMOS module 46 has a preferred length of about 5 mm and a preferred diameter of about 1.2 mm. Other dimensions are also contemplated. The range of dimensions for the housing will depend on the state of technology of the components inside the housing. Today's CMOS sensors are large, as CMOS technology improves diameters for the overall part will decrease. The housing, which is round, is made of a rigid material. The housing can also be made of less rigid materials such as polyimide or heat shrinkable polyethylene terephthalate (PET), which would allow for a thin protective wall. Also, the housing need not be round, it can be oval or other shapes to reduce the overall OD to less than about 1.2 mm. Alternatively, the housing can be left off and the lens, CMOS sensor, and FPC with miniature coaxial cables and optional strain relief can be encapsulated in a protective layer of adhesive that tapers down as it extends proximally as in the embodiment of FIG. 16 discussed below.

The CMOS module 46 is attached to miniature coaxial cables 50 that extend from the proximal end 56 of the CMOS module to the distal end 54 of the connector 52. The cables 50 connect the CMOS module as well as lighting 48 to connector 52. The length and number of cables will depend on the CMOS technology as well as the number of lights used in the system. The cables are shown straight, as an alternative they can be braided, either in part or in whole, to form a tube with an inner wall and an outer wall and distal and proximal ends.

The lighting 48 runs parallel to the CMOS module 46. The lighting can be flush with distal end 44 of the CMOS module or it can sit a distance distal or proximal to the distal end 44 of the CMOS module. By adjusting the placement of the lighting, more or less light will be provided to the CMOS sensor. Alternately, the lighting can be integrated into the CMOS module 46 housing so that it is not separate. The lighting can be obtained from LED, glass or plastic fibers, or other forms of lighting that are adaptable for lighting the area. The lighting may also be a combination of LED and fiber optic. This would allow an additional advantage of the distal tip being capable of being used for treatment options such as laser lithotripsy or optical biopsy.

At the proximal end of the CMOS imaging structure 40 is the connector 52. The connector is used to connect the imaging structure 40 to an interface board/power for LED lighting (not shown). The interface board, which can have format connections such as USB, NTSC, and PAL, can connect to a computer or video processor and monitor loaded with software (not shown) for visual output. The interface board can also be connected to a wireless router (not shown) that can be used to wirelessly transmit the micro-endoscope images to computers, smart phones or even hand held tablets (such as IPads) that have the appropriate applications or software to receive and translate the signals into images. As an alternative, the CMOS module 46 with lighting 48 can be made wireless rendering the coaxial cables and the connector unnecessary.

FIG. 3 illustrates one embodiment of a micro-endoscope of the present invention. The micro-endoscope includes the outer catheter of FIG. 1 with imaging structure 58 at distal portion 70. The assembly includes the CMOS module 46 and lighting 48 (of FIG. 2) that are attached with adhesive 60 to catheter body 12 so that the distal end 16 of catheter body 12 of microcatheter 10 is flush with distal end 44 of the CMOS module 46 and lighting 48. Alternatively, the lighting 48 can be positioned proximally or distally to distal end 44. The combined assemblies are covered with a polymer heat shrink tube 62 that extends from proximal end 64 to distal end 16. The shrink tubing 62 is then heated so that the miniature coaxial cables and the exterior of the outer catheter are brought into close contact with one another for approximately the useable length of the catheter. The shrink tubing 62 forms an outer tube coaxial with catheter body 12. Any shrink tubing can be used, but the preferred is a thin walled super flexible heat shrink tubing made of materials such as Pebax or Polyolefin as sold by Cobalt Polymers (California, USA). The entire length from proximal end 64 to distal end 16 does not have to be covered by a single shrink tubing. Multiple shrink tubings with varying durometers may be used in a sectional or overlapping method or non-shrinkable tube(s) that form a close fit. As an alternate construction, the catheter body 12 of microcatheter 10 can also be assembled leaving off the material layer that makes up the three distinct sections as described in FIG. 1 (proximal section 24, mid section 26, and distal section 28). In this case, the miniature coaxial cables 50 would lie on the reinforcement layer and the shrink tubing 62 would cover the assembly. If needed, strapping to hold the outer catheter and miniature coaxial cables together in the form of short sections of heat shrink tubing such as PET can be applied along the length of the assembly to help with handling prior to shrinking outer cover. The outer cover would then be slid over the entire assembly and shrunk down during manufacture. For either of the above constructions, the outer cover can alternatively be made of a close fitting non-shrinkable plastic or other flexible shaft material.

The remaining free coaxial cables proximal to end 64 can also be encapsulated in a heat shrink tubing or extrusion 66 that may extend to the connector 52. This shrink tubing can be of any durometer or it may already be present as part of the CMOS structure 40 as shipped from the factory. An optional strain relief 68 can be placed over the proximal end of the catheter where the distal end 67 of the free miniature coaxial cables covered in shrink tubing or extrusion and the proximal end 64 of the outer catheter and coaxial cables covered in the polymer cover meet.

The outer catheter with imaging structure 58 can form the outer catheter for a non-deflecting stand-alone micro-endoscope or alternatively can form the outer catheter for the coaxial bi-directional (deflectable) micro-endoscope. In either version, the CMOS structure is mounted external of the outer catheter to thereby minimize the outer diameter of the outer catheter to facilitate insertion and due to the reduced profile, access body structure which might otherwise not be accessible with larger diameter catheters. In the non-deflecting stand-alone versions, in one embodiment by way of example, the inner diameter of the micro-endoscope (i.e., the inner diameter of the outer catheter) will have a working channel sufficient to accept up to about a 4 French (0.052") working device, such as retrieval basket device, laser device, or biopsy forceps. In another embodiment, the working channel will have a diameter small enough to provide an acceptable lumen for tracking a 0.005" guidewire. Also, if used as a stand-alone device, a hydrophilic coating may be added to the outer diameter as well as an RHV on the proximal end to allow flushing and irrigation and/or insufflation of the distal tip. The flushing/irrigation can clean the imaging structure. Note the outer catheter can be tracked over a guidewire.

The visualization system described so far has been using CMOS sensor technology. It is understood that other visualization and/or processing technologies exist including fiber optic, charged-couple device (CCD) sensors, narrow band imaging (NBI), and optical coherence tomography, to name a few. Utilizing one of these options or a combination of a few is considered to be within the scope of this disclosure. These options can be utilized with the non-deflectable as well as with the deflectable micro-endoscope embodiments disclosed herein.

An alternate embodiment of the micro-endoscope is shown in FIG. 4. The micro-endoscope has imaging structure 72 at distal portion 74. Construction is much the same as FIG. 3 except that the CMOS module 46 and the lighting 48 are free of the shrink tube 62 so that distal end 44 of the CMOS module 46 and lighting 48 are distal of the distal catheter end 16. The CMOS module is shown unattached in FIG. 4, however, it should be appreciated that in assembly the CMOS module will be attached to an inner catheter extending through a lumen in catheter body 12 such as in FIGS. 7-9 discussed below.

FIG. 5 illustrates one embodiment of a coaxial bi-directional micro-endoscope 76 with distal deflectable portion 86. In the embodiments herein where the micro-endoscope tip can be deflected, this is achieved through the interaction of the inner and outer catheters and the column member attached to the inner catheter which is surrounded by a lateral reinforcement tube. This is described in detail below.

Turning to the embodiment of FIGS. 5-6D, coaxial bi-directional micro-endoscope 76 includes the outer catheter of FIG. 3 (designated by reference numeral 117) fitted with a rotating hemostatic valve (RHV) 78, an inner catheter assembly 80 slidably disposed in the outer catheter inner lumen, a distal coil 98, and marker band 100. It also includes imaging structure which is similar to imaging structure 58 of FIG. 3. The coil 98 is preferably a helically wound flexible coil. The coil may be made from a polymer, metal or combination thereof, but the preferred coil material is platinum/iridium for radiopacity. In addition, it can be made of a solid tube, either plastic or metal with or without laser cutting to introduce flexibility. Marker band 100 can be a solid tube or a flexible helical wound coil. Either option can be made from a polymer or metal, the preferred material is platinum/iridium for radiopacity.

The inner catheter body 82 of inner catheter 80 runs from proximal end 94 to distal end 96 and is configured with an outer diameter capable of being slidably positioned inside the outer catheter. The overall useable length of inner catheter 82 can range from as short as 0.25 feet to greater than 18 feet with a preferable length between approximately 15 cm (0.5 feet) to 400 cm (13 feet). Catheter body 82 extends a distance past distal end 16 of outer catheter 12 to distal end 96. The distal exposed end of the inner catheter 80 is configured for deflection and covered with a coil 98 that extends from outer catheter distal end 16 to distal end 102. The distal deflectable portion 86 can include a marker band 100 at the very distal end attached to coil 98 and/or underlying inner catheter portion. The length of the distal deflectable portion will be based on the length of the exposed inner catheter. In one embodiment, the distal exposed end of the inner catheter can range from approximately 5 to approximately 9 mm resulting in a bend radius of approximately 3.5 mm. The preferred bend radius will depend on the need for which the coaxial bi-directional micro-endoscope is designed.

The proximal end of inner catheter assembly 80 includes a winged hub (luer) 90 and optional strain relief 92 coupled to catheter body 82. Attached to winged hub 90 is RHV 88 with side arm 84 and end cap 83. End cap 83 allows access to the working channel of the inner catheter 80 of the coaxial bi-directional micro-endoscope for passage of guidewires, forceps, or other accessories needed for carrying out diagnostic or therapeutic functions. In one embodiment, the inner diameter of the inner catheter assembly 80 will have a diameter sufficient to accept up to a 4 French (0.052") working device, such as retrieval basket, cutting wires, or biopsy forceps. In another embodiment, the working channel will have a diameter small enough to provide acceptable tracking for a 0.005" guidewire. Side arm 84 allows flushing and irrigation and/or insufflation.

The largest outer diameter for the coaxial bi-directional micro-endoscope 76 will be in the distal portion where the CMOS module 110, catheter body 82, and polymer shrink tubing 119 come together. As noted above, the imaging structure can be the same as imaging structure of FIG. 3. In some embodiments, the distal portion of the micro-endoscope 76 has an outer diameter that can range between approximately 3 French and approximately 14 French, and preferably between approximately 4.5 French and approximately 10 French.

The proximal winged hub 104 on the outer catheter 117 is fitted with RHV 78 with end cap 106 and side arm 108. The purpose of end cap 106 is to provide a lock for holding the inner catheter 80 in position. That is, end cap 106 can be rotated in a first direction to clamp and secure the inner catheter 80. The purpose of side arm 108 is to provide access to the inner lumen formed between the coaxial inner and outer catheters so lubrication, irrigation, and/or insufflation can be introduced. In the deflectable micro-endoscope embodiments which utilize relative movement of the inner and outer catheters to deflect the distal tip, lubrication can be provided during the procedure to provide smoother movement of these components and thereby facilitate deflection. Fluid introduced through side arm 108 can exit holes 111 in the outer shaft or gaps 99 in distal tip coil 98. The RHV 78 is one example of a locking/lubrication system for the coaxial bi-directional micro-endoscope. Other designs may be used to accomplish the same goals.

As noted above, the outer catheter is one part of the overall assembly of the coaxial bi-directional micro-endoscope 76. Likewise, the outer catheter can be added as an outer shaft to existing medical devices such as endoscopes, deflectable (micro) catheters employing push/pull wires, balloon catheters. In that case, the catheter 10 can optionally be eliminated and imaging structure 40 can be placed directly on the outer diameter of the alternate device using the polymer shrink tubing 62 or another close fit polymer tube.

FIG. 6A shows an enlarged top view of distal deflectable portion 86 of the coaxial bi-directional micro-endoscope 76 of FIG. 5 being deflected. When the end cap 106 on RHV 78 is in the open position, the inner catheter 82 is free to move relative to the outer catheter. The back and forth axial motion causes the distal tip 112 to deflect as described in more detail below. The distal tip 112 may be locked in position at any point by tightening the end cap 106 which locks the inner catheter 82 in position. Also, the tip is shown deflecting perpendicular to the CMOS module 110. This is shown as an option. The CMOS module 110 can be placed at any position or orientation relative to the deflectable tip.

The deflection structure 113 used to deflect distal portion 86 is shown in FIGS. 6B-6H. The deflection structure is comprised of the outer catheter 117, inner catheter 82, column 121 and lateral (axial) reinforcement (support) tube 125. Also, a deflectable marker band 115, spiral cut tube 119, and marker band 123 are provided.

In assembly, marker band 115 is inserted mid-way into the distal end of outer catheter body 117 and bonded to form a lip. Inner catheter 82 has a distal spiral cut tube 119 at its distal end and is inserted through outer catheter 117 and marker band 115 until it extends a distance past the distal end of outer catheter 117 and marker band 115. The proximal end of column 121 is attached either to the surface of marker band 115 or inserted into the distal end of outer catheter 117 between the marker band 115 and the inner lumen of the outer catheter 117 and then attached. The distal end of column 121 is attached to the distal end of spiral cut tube 119 of inner catheter 82 using marker band 123.

The underlying column theory used to deflect distal section 86 will now be described with reference to FIGS. 6C and 6D. Without a lateral (axial) reinforcement (support) tube 125, which in the embodiment of FIG. 6D is a coil, when a proximal pull force is applied to inner catheter 82 to move inner catheter 82 proximally (or alternatively when outer catheter 117 is moved distally, or both catheters are moved in these directions relative to each other), spiral cut tube 119 will be pulled proximally resulting in attached column 121 compressing (FIG. 6C). However, when lateral reinforcement tube, e.g., coil 125, is added to deflection structure 113 to surround column 121, and the same proximal axial force is again applied, the distal tip, which can no longer compress, will deflect due to the reinforcement tube (coil) as shown in FIGS. 6D and 6E. Note column 121 contacts an inner wall of tube 125 during deflection. If the inner catheter 82 is moved axially distally (or alternatively when outer catheter 117 is moved axially proximally or both catheters are moved in these directions relative to each other) the column 121 will bend and the distal tip will deflect in the direction of the tip as shown in FIG. 6F. Note column 121 will again want to contact the inner wall of tube 125, however, in this case, lateral reinforcement tube 125 will serve more to keep components together in the bend. Such tip deflection is shown in FIGS. 6G and 6H. Note that by varying the dimensions, i.e., cross-sectional dimension, or materials or cuts, of the column 121 the load to deflect the distal tip can be increased or decreased. For example, increasing the dimensions will increase the force required to deflect the distal tip. Note though if the column dimensions become too thin, the column will become unstable leading to multiple buckling points under load. This will result in little or no tip deflection. Further details of the column theory are discussed below.

Note, in these Figures, the tip of the inner catheter deflects while the tip of the outer catheter does not deflect or substantially deflect.

The marker bands 115 and 123 can be made of any metal or a polymer tube or coil with a preferred material of platinum/iridium. The deflection structure 113 can even be designed leaving these parts out or in combination with the column 121. The preferred cross section of column 121 is non-circular, and preferably rectangular, so deflection occurs in the desired plane, however other shapes such as round can be used. Also, cuts or other features can be added to the column to influence movement. The column 121 can be made of any metal or metal alloy and even a plastic, however the preferred material is a super elastic nitinol or spring tempered stainless steel wire or rod. Spiral cut tube 119 need not have a spiral cut pattern. It can have any laser cut pattern that will influence flexibility. It can also be made of any metal, polyimide or plastic but the preferred material is super elastic nitinol or spring tempered stainless steel. The tube may also be coated in a thin polymer and contain a lubricious inner liner. Alternatively, the tube can also be made of a coil or a braid that may include some plastic or a solid plastic tube. The cuts will affect the load to deflect the tip.

Figure 7:
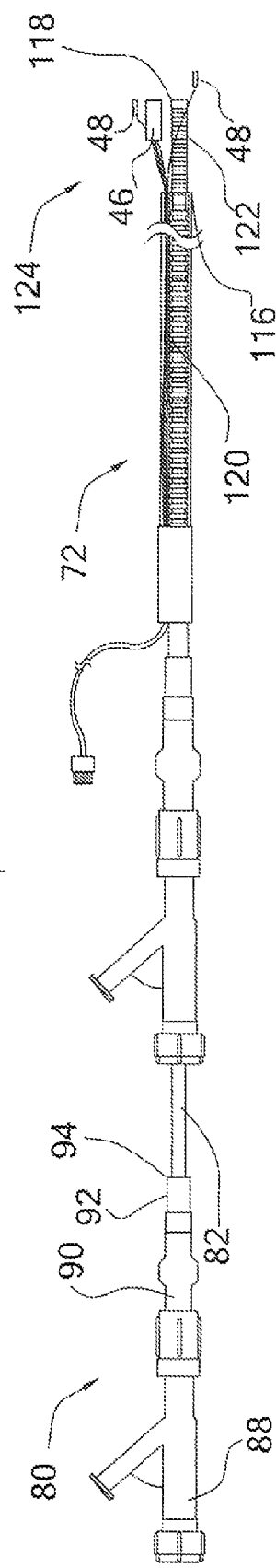
FIG. 7 illustrates a coaxial bi-directional micro-endoscope in accordance with another embodiment of the present invention which includes the outer catheter of FIG. 4 and the inner catheter of FIG. 5 (the CMOS module shown unattached for clarity)

FIG. 7 illustrates another embodiment of a coaxial bi-directional micro-endoscope 114 assembled with an outer catheter (e.g., the outer catheter of FIG. 3), an imaging structure 72 and inner catheter 80. Inner catheter 80, which in this embodiment is the same as inner catheter 80 of FIG. 5, is shown placed inside the outer catheter. In this embodiment, the CMOS module 46, lighting 48, and a portion of miniature coaxial cables 120 extend distal of distal end 116 of the outer catheter so that they can be mounted at the distal end 118 of deflecting tip 122.

Figure 8:
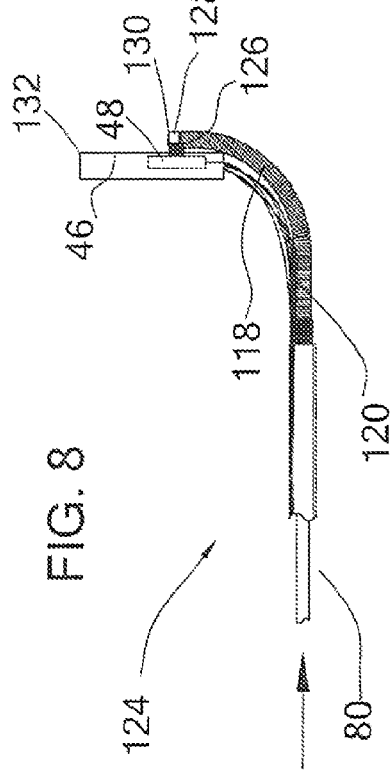

In one mounting method, shown in FIG. 8, CMOS module 46 and lighting 48 of coaxial bi-directional micro-endoscope 114 are mounted parallel to deflecting tip 118 at distal portion 124. They are held in place with adhesive or solder 126 near optional marker band 128. The cables are designated by reference numeral 120. The distal end 132 of CMOS module 46 extends past the distal end 130 of the catheter 80. The offset between the distal end 130 of the catheter and the distal end 132 of the CMOS module is so that the hard housing of the CMOS module 46 will not affect deflection. The lighting 48 is also shown offset to the distal end 132 of the CMOS module 46, not flush. This is just an example of placement. Lighting can be placed at any location that will most benefit the CMOS module 46.

Figure 9:
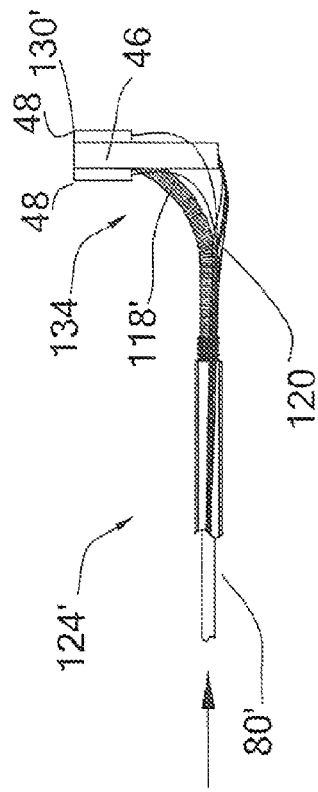
FIG. 8 is an enlarged side view of the distal portion of the coaxial bi-directional micro-endoscope of FIG. 7 with the CMOS housing mounted parallel to deflection and FIG. 9 is an enlarged side view of the distal portion of an alternate embodiment of the coaxial bi-directional micro-endoscope with the CMOS housing mounted perpendicular to deflection.

An alternate mounting method is shown in FIG. 9 wherein a perpendicular mounting of the CMOS module 46 and lighting 48 relative to deflecting tip 118' on distal portion 124' distal of inner catheter 80' is illustrated. In this embodiment, CMOS module 46 and lighting 48 are mounted flush to the distal end 130' and perpendicular to the deflecting tip 118'. This mounting causes the CMOS module 46, lighting 48 and the miniature coaxial cables 120 to kick out so as not to affect deflection.

Figure 10:
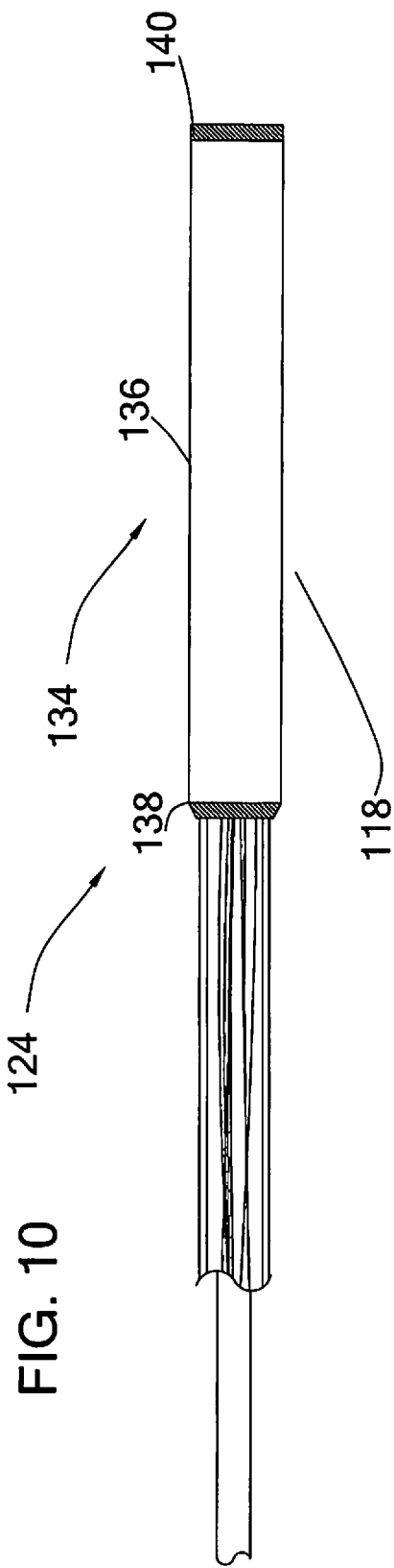
FIG. 10 is an enlarged side view of the distal portion of another embodiment of the coaxial bi-directional micro-endoscope with the CMOS housing mounted perpendicular to deflection and having an outer cover.
Figure 10A:
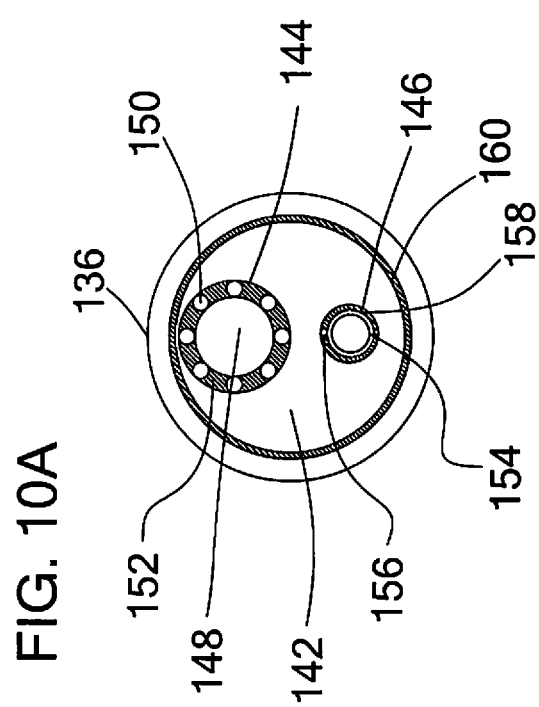
FIG. 10A is an enlarged front view of the distal tip of the coaxial bi-directional micro-endoscope of FIG. 10 showing a two lumen band with integrated lighting around the CMOS module.

A cover 136 can be utilized (not deflecting) with a perpendicular mounting as shown in FIGS. 10 and 10A. The cover 136 extends from proximal end 138 to distal end 140 and covers entire deflecting tip 118. The cover may extend over the outer catheter with polymer cover, if desired. The cover 136 is preferably made from a highly flexible material such as polyisoprene but can be made of other polymers such as HDPE, LDPE, CFlex, latex, silicone, nitrile, pebax, nylon, or polyurethane. If a solid non-flexible type polymer tube is used, laser cut holes or cuts can be introduced to allow fluid introduced through the RHV to flow out. As an alternative, a balloon like polymer can be used as cover 136. In this case, fluid introduced through the RHV would cause inflation. The cover 136 can also be made from a coil or laser cut metal (for flexibility) using metals such stainless steel, nitinol, platinum/iridium, or even fibers.

In this embodiment, all of the components are integrated into marker band 142, which has two lumens, lumen 144 and 146. The marker band 142 may be made from metals such as stainless steel, platinum/iridium or even plastics such as HDPE, LDPE, or Pebax. These are just examples of different options for providing a two lumen structure.

Lumen 144 contains CMOS lens 148 and several lighting fibers 150 arranged in a ring around lens 148. Lens 148 and lighting fibers 150 are joined to marker band 142 with adhesive 152. The lighting 150 can be from a variety of sources such as LEDs and/or fibers made of glass, quartz or polymers. As an alternate, the ring of lights can be used for both lighting and as a laser source for treatment options such as lithotripsy or optical biopsy. This is done through configuring the laser source to switch back and forth between lighting and firing or by including dedicated lithotripsy or biopsy fibers in the ring next to the lighting fibers.

Lumen 146 of marker band 142 contains the inner lumen 154 of the inner catheter 154. This is the working channel (lumen) of the coaxial bi-directional micro-endoscope through which guidewires and accessories are introduced for gastroenterology (GI) or ear, nose throat (ENT) procedures, for example. Above the inner lumen 154 is the column 156, which as described above is used in deflection of the distal tip. The column 156 and inner lumen 154 are bonded together with adhesive 158. Surrounding the marker band 142 is cover 136, which is bonded to marker band 142 with adhesive 160. If desired, cover 136 can stop proximal of the marker band 140 so as not to cover it.

FIGS. 11 and 11A illustrate a top view of an alternate embodiment of a coaxial micro-endoscope 161 having a dual (two) lumen outer catheter and an imaging capability assembly. The micro-endoscope includes outer catheters 164 and 166, CMOS module 168, and miniature coaxial cables 169, all encapsulated by polymer cover 171. Extending from the proximal end of polymer cover 171 is polymer cover 173, which is coupled to connector 177. An optional strain relief (not shown) covering distal end of cover 173 and proximal end of cover 171 could be provided. Coupled to the proximal end of catheters 164 and 166 is tri-furcate hub 170 with optional strain relief 172. This embodiment allows the micro-endoscope to have two working channels (lumens). One channel can be used for irrigation and/or insufflation while the other can be used for GI or ENT treatment options, for example. Other lumens may be added for additional irrigation or a shorter lumen can be added to make the coaxial bi-directional micro-endoscope into a rapid exchange device. Alternately, a polymer multi-lumen extrusion or metal tubing can be used as a substitute for the combining separate catheters. This may be variable stiffness or just a single durometer. Outer catheters 164 and 166 can be formed as separate tubes attached together or formed as a single tube with two lumens.

Tri-furcate hub 170 has two side arms, 174 and 176, and end cap 178. Side arm 174 is for access to the inner lumen of catheter 164 and can be used for introduction of accessories or irrigation/insufflation. Side arm 176 is for access to the inner lumen of catheter 166 and can also be used for introduction of accessories or irrigation/insufflation. End cap 178 is for used for locking an accessory within the inner lumen 166 as well as access to the inner lumen through which the inner catheter assembly can run. Tri-furcate hub 170 can be replaced with a molded part designed to do the same functions. It can be molded out of plastic or machined of metal.

The CMOS module 168 is placed on top of catheter 164 and catheter 166 with lighting 180 and 182 on either side of the CMOS module 168. All of the components can be bonded by adhesive 184 and surrounded by polymer cover 171. If desired, one lighting unit (for instance 180) can be used for laser treatments such as lithotripsy or visualization using narrow band imaging while the other (182) is strictly for lighting. The lighting can come from LED, fibers, or other adaptable sources. Also, although most embodiments have mentioned using CMOS as imaging system, module 168 can be any imaging technology, such as CCD, fiber optics, narrow band, or optical coherence tomography to name a few.

FIG. 12 illustrates an alternate embodiment of the dual lumen coaxial bi-directional micro-endoscope with imaging capability. The micro-endoscope 186 includes an outer catheter assembly 162 including two outer catheters (tubes) 164 and 166 positioned side by side as in FIG. 11, inner catheter assembly 185 extending through one of the outer catheters, coil 188 which forms the lateral reinforcement member for the column, and marker band 190 at distal end 192. The coil 188, which forms the lateral reinforcement member for the column, covers the exposed distal end of inner catheter 185 and deflection components (not shown), e.g., the column member, attached to outer catheter 166 and extending distally therefrom. Coil 188 extends distal of distal end 194 of outer catheter 166 of outer catheter assembly 162 to distal end 192. The coil 188 can sit directly on outer catheter 166 or near the end of it. The preferred material for the coil is platinum/iridium but any metal, plastic or combination of both can be used. Laser cutting may be used on solid tubing to cut slots to increase flexibility and bending. Coil 188 does not cover distal end 196 of catheter 164.

In an alternate embodiment of the dual lumen coaxial bi-directional micro-endoscope with dual lumen deflecting tip, both catheters/lumens are deflectable. In this embodiment (FIG. 13), micro-endoscope 198 has a coil 187, forming the lateral reinforcement tube for the column member, which extends from the distal end 196 of outer catheter 164 and distal end 194 of outer catheter 166 to distal end 192. This creates a dual lumen deflectable tip. Deflection in the embodiments of FIGS. 12 and 13, as well as in the other embodiments disclosed herein, are achieved in the same manner as discussed above, i.e., the column 121/coil 125 of FIGS. 6D and 6G.

Figure 14:
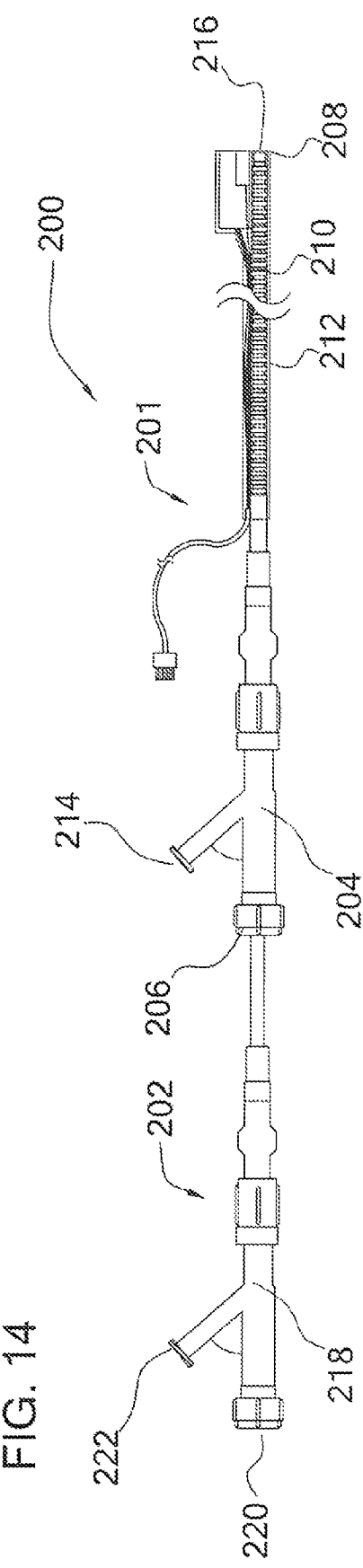
FIG. 14 is a side view of another embodiment of a non-deflectable coaxial micro-endoscope similar to the embodiment of FIG. 5 and having drainage holes.

FIG. 14 illustrates another embodiment of a non-deflectable coaxial micro-endoscope 200. It includes inner catheter assembly 202 with RHV 218, and an outer catheter 212 with imaging structure 201 and RHV 204. The outer catheter 212 can be the same as the outer catheter of FIG. 5. The inner catheter assembly 202 and outer catheter are lined up so they are flush at distal end 208.

Attached to the proximal end of inner catheter assembly 202 is RHV 218 with side arm 222 and end cap 220. End cap 220 allows access to the working channel of the inner catheter 202 of the micro-endoscope 200 for passage of guidewires, forceps, or other accessories needed for carrying out diagnostic or therapeutic functions. Side arm 222 allows flushing and irrigation and/or insufflation through the distal tip. As mentioned above, this flushing, as in the other embodiments disclosed herein, aids visualization.

Attached to the proximal end of outer catheter 212 is RHV 204. Side arm 214 on RHV 204 is used for lubrication of the inner lumen as well as for irrigation/insufflation of the distal tip through laser cut holes 210 in the outer catheter 212. Such irrigation can aid visualization. In addition, fluid/air will also exit distal tip 216. If a larger working channel is needed, the inner catheter assembly 202 can be removed proximally by unlocking end cap 206 and withdrawing inner catheter 202 from outer catheter 212. This will make the micro-endoscope a single lumen device with a larger internal diameter for introduction of devices therethrough. Such removability is also applicable to the other embodiments disclosed herein where the imaging structure is attached to the outer catheter.

Figure 15:
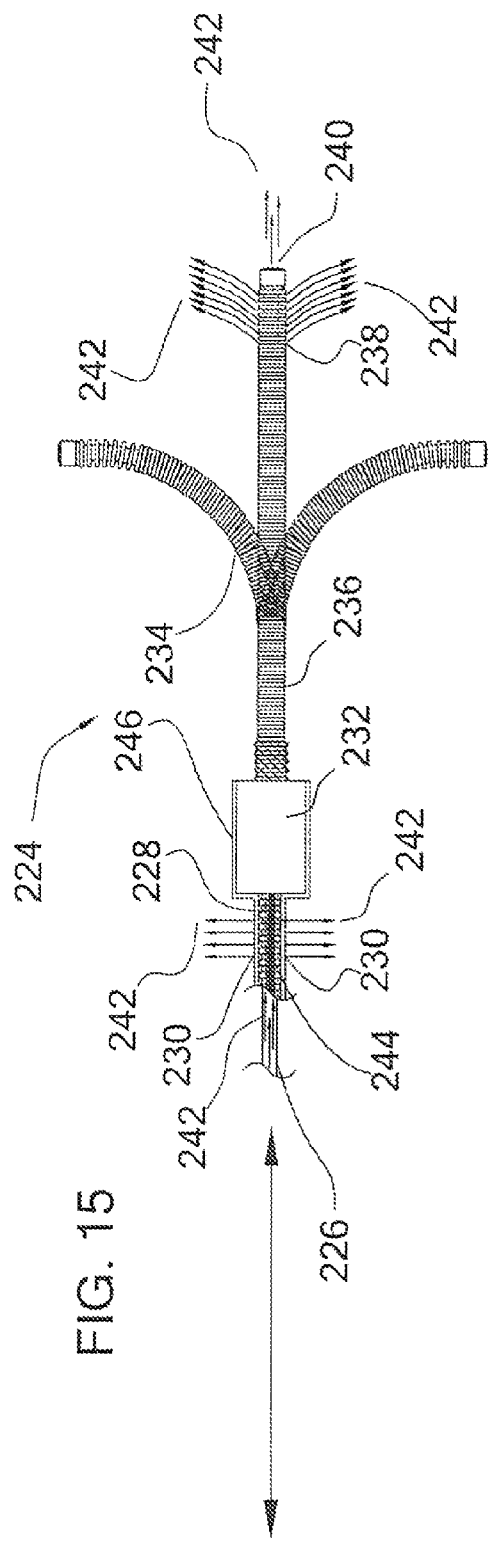
FIG. 15 illustrates an enlarged top view of a distal portion of another alternate embodiment of a coaxial bi-directional micro-endoscope configured with exit ports at its distal end.

FIG. 15 illustrates distal portion 224 of another embodiment of a deflecting coaxial bi-directional micro-endoscope. It includes inner catheter 226, outer catheter 228 with laser cut holes 230, CMOS module 232 with miniature coaxial cables 244, polymer cover 246, distal deflecting tip 234 with coil 236 having gaps 238, and distal end 240. When fluid 242 is introduced through an RHV (not shown but preferably the same as the RHV of FIG. 14) connected to the proximal end of outer catheter 228, it will exit holes 230, gaps 238, and distal end 240. This will provide irrigation for clearing material in front of the CMOS module and help prevent clouding during image acquisition. The flushing can occur at any point during deflection or it can be continuous. The holes and gaps also allow optional insufflation.

Figure 16:
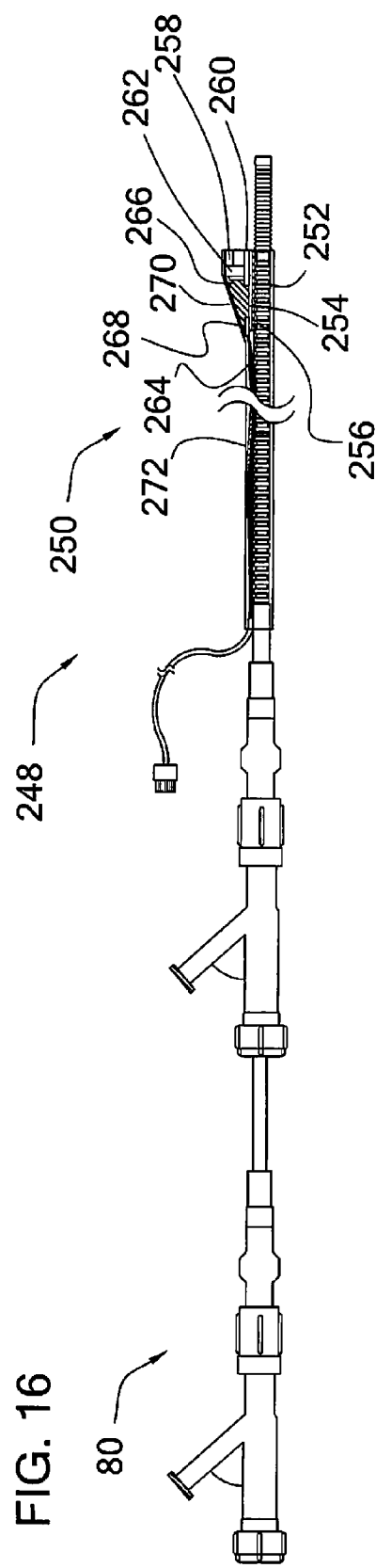
FIG. 16 illustrates an alternate embodiment of a coaxial bi-directional micro-endoscope with CMOS module housing replaced with an adhesive.

Another embodiment of the coaxial bi-directional micro-endoscope is designated by reference numeral 248 and illustrated in FIG. 16. The distal portion 250 includes outer catheter 252, flexible printed circuit (FPC) 254, adhesive 256, lens 258, lighting 260, CMOS sensor 262, optional strain relief 268, coaxial miniature cables 264, an adhesive barrier 266, and polymer cover 270. FPC 254 has lens 258, CMOS sensor 262, coaxial miniature cables 264, and option strain relief 268 attached thereto. The FPC 254 is attached to outer catheter 252 and lighting 260 with adhesive 256. The FPC 254 with attached components is encased in adhesive barrier 266, which has taper 270 that tapers from distal to proximal. The approximate usable length of the outer catheter, including distal tip with FPC and components, is covered with a polymer cover 272. The purpose of the adhesive barrier 266 is to provide an alternative to the round housing such as in FIG. 14 to protect the FPC 254 and its attached components. It addition, it tapers down proximally removing the square edge of the housing. If a rigid housing is used instead of adhesive barrier 266, a tapered part can be inserted proximal to the proximal edge of the housing to remove the step. A protective shrink tubing such as PET or thin walled polyimide can also be used as a substitute for the housing. In addition, the FPC 254 can be curved with rounded edges. This will allow it to sit on the catheter outer diameter more firmly and remove sharp edges that may cut heat shrink tubing. Note the aforedescribed structure can be utilized with the outer catheter used in the non-deflecting as well as in the deflecting tip embodiments.

Figure 17:
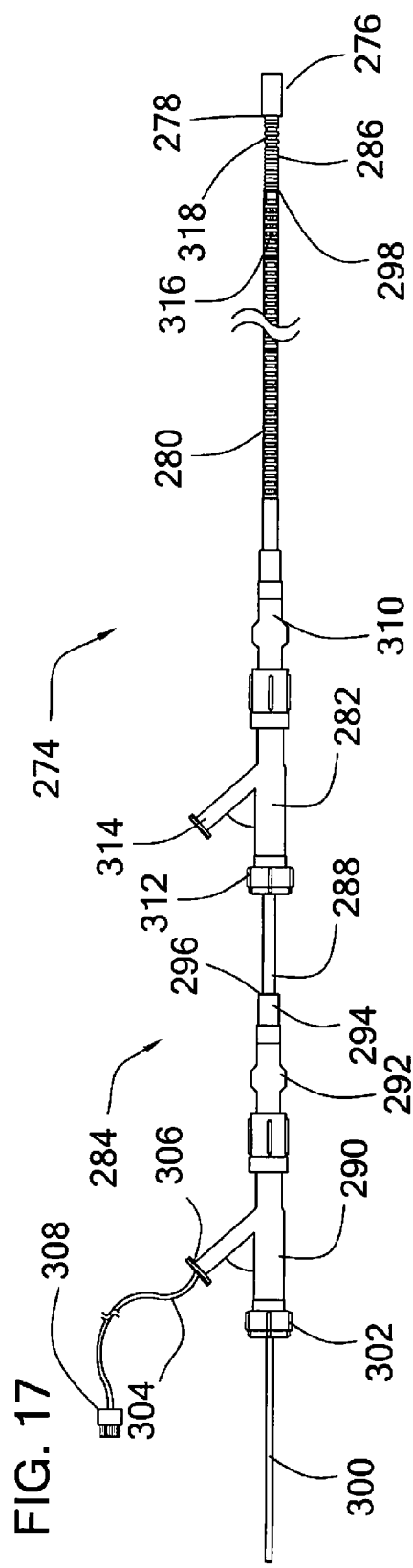
FIG. 17 illustrates another embodiment of a coaxial bi-directional micro-endoscope with CMOS module attached to the distal tip of the micro-endoscope.

An alternate embodiment of a coaxial bi-directional micro-endoscope 274 with CMOS module and integrated lighting 276 mounted at the distal end 278 is shown in FIG. 17. Such mounting can be utilized with non-deflecting and deflecting versions of the microendoscope. Micro-endoscope 274 includes an outer catheter 280 fitted with rotating hemostatic valve (RHV) 282, an inner catheter assembly 284 disposed in the outer catheter inner lumen, a distal coil 286, and CMOS module and integrated lighting 276. The inner catheter assembly 284 includes catheter body 288, RHV 290, winged hub (luer) 292, and optional strain relief 294. The catheter body 288 runs from proximal end 296 to distal end 278 and is configured with an outer diameter capable of being positioned inside the outer catheter 280. Inner catheter body 288 extends a distance past outer catheter distal end 298 to distal end 278. The distal exposed end of the inner catheter 288 is configured for deflection (not shown) in the same manner as in FIGS. 6D and 6G and is covered with a coil 286 that extends from outer catheter distal end 298 to distal end 278 and forms a lateral reinforcement (support) tube for the column. A removable wire 300 can be utilized, extending through the inner lumen of inner catheter body 288 for support to aid in introducing and pushing the micro-endoscope 274. The wire 300 can be locked in place with rotational end cap 302 which when rotated in one direction clamps wire 300.

The proximal end of the miniature coaxial cables and lighting are covered in plastic 304 (either extrusion or shrink tubing) and extend out of side arm 306 on RHV 290 and connect to connector 308. If desired, the cables and cover can be glued in place in arm 306. The distal section of the miniature coaxial cables run through the inner lumen of the inner catheter body 288 and exit distal end 278 where they are attached to the CMOS module and lighting 276, which is glued or soldered in place to coil 286. The attachment could be similar to that of FIG. 20A or 21A.

The proximal winged hub 310 on outer catheter 280 is fitted with RHV 282 with end cap 312 and side arm 314. The purpose of end cap 312 is to provide a lock for holding the inner catheter assembly 284 in position. When end cap 312 is opened, the inner catheter assembly 284 is free to move axially back and forth resulting in deflection of the CMOS module 276 in the manner described above and shown for example in FIGS. 6D and 6G. The purpose of side arm 314 is to provide access to the inner lumen formed between the coaxial inner and outer catheters so lubrication/irrigation and/or insufflation can be introduced. Distal exit ports 316 can be laser cut into the shaft or gaps 318 can be made in coil 286 for the fluid and/or air to exit. The RHV 282 is one example of a locking/lubrication system for the micro-endoscope. Other designs may be used to accomplish the same goal.

FIG. 18 illustrates an embodiment of a coaxial bi-directional micro-endoscope visualization system 320. Visualization system 320 includes coaxial bi-directional micro-endoscope 322 with connector 52, interface board/LED power source 324, USB connector and cable 326, and computer 328 loaded with visualization software. The micro-endoscope illustrated is the embodiment of FIG. 5, but the other micro-endoscopes disclosed herein can also be used with the visualization system 320. In use, a coaxial bi-directional micro-endoscope 322 with connector 52 is removed from packaging. Connector 52 is connected to interface board/LED power source 324, which is in turn connected to a computer 328 or video processing/monitoring/recording system loaded with necessary software using USB connector and cable 326. Once the visualization system is ready, a guidewire is inserted through the working channel of coaxial bi-directional micro-endoscope 322 and the combined assembly is inserted into the working channel of a larger endoscope for tracking to the area of interest inside the body. Once there, images can be viewed and recorded. If needed, the working channel of the micro-endoscope can be used for diagnostic and/or therapeutic procedures once the guidewire is removed. When the end cap on the outer catheter's RHV is open, movement of the inner catheter body (or outer catheter relative to the inner catheter) will result in deflection as described above. Irrigation and/or insufflation can be introduced through the side arm on the outer catheter RHV. After the procedure is completed and the device is removed, connector 52 is disconnected from interface board/LED power source 324 and the coaxial bi-directional micro-endoscope 322 can either be discarded or cleaned using appropriate methods depending on whether it is designed as a disposable or re-usable or re-sterilizable device. Although interface board/LED power source 324 is shown connected to a computer 328 using USB connector and cable 336, other connectors and formats can be used, for instance NTSC or PAL to connect to other viewing options so long as they have the appropriate software. Also, the power source for the LED lights can be a separate component that is self-powered (battery) or plugged into a wall socket. The steps described above for preparation and use of the coaxial bi-direction micro-endoscope are only an example of how the scope can be prepared and used. They are not meant to be the standard. For instance, the guidewire may be optionally left out if tracking is not required of the device or the coaxial bi-directional micro-endoscope can be used as a standalone device not requiring another endoscope.

FIG. 19 illustrates an alternate embodiment of a coaxial bi-directional micro-endoscope visualization system 330. Visualization system 330 includes coaxial bi-directional micro-endoscope 322 with connector 52, and wireless router/LED power source 332. The micro-endoscope illustrated is the embodiment of FIG. 5, but the other micro-endoscopes disclosed herein can also be used with the visualization system 330. In use, the coaxial bi-directional micro-endoscope 322 is connected to wireless router 332 by connector 52. The wireless router would transmit signals received from the coaxial bi-directional micro-endoscope 322 to any system that has the appropriate software for receiving and viewing and/or recording. Examples include, but are not limited, to a computer 328, tablet (iPad) 336, or smart phone 334. As an option, additional software and applications can be developed for the coaxial bi-directional micro-endoscope. An example is an application combining the visual data from the CMOS module with the radiographic data from fluoroscopy.

FIGS. 20A-20C illustrate a coaxial bi-directional micro-endoscope 337 with distal portion 338, similar in construction to coaxial bi-directional micro-endoscope 274 shown in FIG. 17 except in this embodiment, the lighting used for illumination for CMOS camera 340 mounted at distal end 342 is optical illumination fibers 344. As stated earlier, the fibers may be made of glass, plastic or other material used for making optical illumination fibers. For this embodiment, the preferred fiber is made of polymer or plastic with an outer diameter of around 0.010" to 0.020". More or less than two fibers can be used as well as different diameter or shaped fibers or mixed fiber materials. Additionally, the camera may have a lens, which may be round, square or other shape, made of glass, polymer, quartz, or combined materials. The lens can be added to the camera before the tip is assembled in-house using typical endoscope or camera manufacturing methods or it can be shipped from the manufacturer in place.

The fibers 344 are mounted below the camera 340 and above the inner lumen 346, as shown in FIG. 20B. A cover 348 is placed over camera 340, fibers 344, and inner lumen 346 (shown with guidewire 347 positioned therein) and encased in epoxy or adhesive 350. The cover 348, which for example, may be made of metal, plastic, or shrink tubing runs from distal end 342 to proximal end 352. In addition, if the cover is a band or a laser cut tube, it may have holes for adding glue to inner contents and a slot for sliding the camera body into. Also, although the cover 348 is shown round, it can be other shapes such as oval or square to minimize dimensions. The edge between the proximal edge 352 of the cover 348 and outer coil 354 may be taken off by the application of adhesive or solder 356 around the edges. Alternatively, the epoxy or adhesive under the cover can be left out or used to tack parts and the entire distal assembly can be encased in plastic melted down to form an cover using removable heat shrink tubing. This cover may be more oval than round due to parts being squeezed together. Once assembled, and, if necessary, the distal tip can be polished. In some instances, polishing may not be required. The fibers run through the catheter from distal end 342 to proximal end 358 where they are glued into connector 360 and polished. The manufacturing description provided for polishing distal and proximal ends is merely exemplary and not limiting on how the final device is assembled in manufacturing.

FIG. 20C shows a side view of the distal portion 338 with the outer coil 354 in cross section and cover 348 removed to better understand camera mounting. As shown in FIG. 20C, the camera 340 is connected to a flat ribbon power and data cable 362 that runs through the catheter from the camera's proximal end 364 to the end 366 (FIG. 20A) where it is attached to a USB type connector 368. The cable 362 is outside the inner catheter. The flat ribbon power and data cable 362, as used by Awaiba (Germany) to connect the NanEye CMOS camera head to the USB base station (not shown) may have cross sectional dimensions around 0.72 mm wide (0.0283") and 0.188 mm (0.0074") thick. To make the ribbon more conformable to the inner lumen of the outer catheter or any cover tube, the ribbon may be cut in two to create two separate groups of wires. Alternatively, the wires can be separate from one another as shown in earlier drawings. Also, in order to reduce device distal outer diameter further, a thin walled tube can be inserted into the distal end of inner diameter of inner catheter and glued in place. The camera and lighting can then be glued on that structure with cover tube.

As shown in FIG. 20C, the flat ribbon 362 is configured so that the thin dimension is parallel to the thin dimension of the column 370 which has a free length L of about 6 mm, although other dimensions are contemplated. This configuration allows for optimal bending. The column 370 shown in this particular configuration is made of spring-tempered stainless steel, however other materials such as Nitinol can be used. The column is 0.002" thick and 0.006" wide but, depending on what is being deflected, can be made thicker or wider and even round. The column 370 is covered by a reinforced (support) tube in the form of outer coil 354 and together function to effect deflection according to the column theory described herein. Column member 370 is attached to marker bands 372 and 374. Marker band 374 is positioned so it extends partially from outer catheter 337 to form a lip on which the coil 354 proximal end is glued in place (glue not shown). Inner catheter 339 runs through marker bands 372 and 374 where its distal end is aligned with the fibers and camera. Both the ribbon and the fibers run under distal marker band 372 and through proximal marker band 374 where they enter the inner diameter of the outer catheter 337. The inner catheter distal end, fibers and the camera can be tacked in place at distal end (not shown) to hold alignment before a cover (not shown) is added. Alternatively, a cover can be added and glue can be wicked in.

Inside the outer catheter 335, the data cable and fibers can be held in contact with the outer diameter of the inner catheter 339 using flexible plastic tubing, polyimide tubing, bands at set distances, glue, or other by other tacking methods. The fibers and data cables can also be left free to float inside the outer catheter inner diameter. Note, if an outer tubing (such as polyimide) is used to keep the fibers/flat ribbon power and data cable and inner catheter together, it may be set a sufficient distance proximal of the deflection section of the catheter so as not to interfere with the push deflection. The distance may be about 1 cm or greater from distal end 342. Glue joints should be applied to the distal and proximal ends of the outer tubing so as to join the tube with the inner contents, allowing them to move as a unit with the inner catheter. If the outer tubing has to run through the deflection area, it should be laser cut to allow bending.

The fiber and the flat ribbon cable exit the proximal end of the catheter assembly through arm 376 of RHV 378 where they are covered with the flexible tube 380. RHV 378 is purely exemplary, the handle can be molded or designed to fit the design need. In addition, although all movement has been shown to be purely axial, the proximal handle can be fitted with a screw system making proximal movement rotational to bring about axial deflection. Tube 380 may be made of a spiral cut PTFE or other highly flexible tubing. A connector 382 at the proximal end of tube 380 connects to a bifurcation member 384 to separate the fibers from the cable. The fibers and cable each have a cover tube 386 and, if necessary, strain relief covers (not shown). Additionally, stainless steel mandrels (not shown) may be added to the inside of the cover tubes to help with any bending due to the weight of the connectors. The above dimensions, materials, and construction shown are exemplary and are not limiting in any way. In addition, the catheter may be assembled in sub-assemblies and assembled into a full catheter using interventional catheter manufacturing techniques combined with laser fiber catheter or endoscope techniques.

In an alternate embodiment, the spiral tube is not provided and the data cable 362 can be used to deflect the distal tip. That is, the cable can be attached to a distal end of the column moved axially proximally or distally relative to the outer catheter 335, and thereby function to effect deflection in the same manner as the axially movable inner catheters described herein effect deflection due to the interaction of the column 370 and outer reinforcement coil 354 (or tube). This can also be achieved by use of a laser fiber or other imaging component attached to the column member movable to deflect the tip. This is discussed below.

Figure 21A:
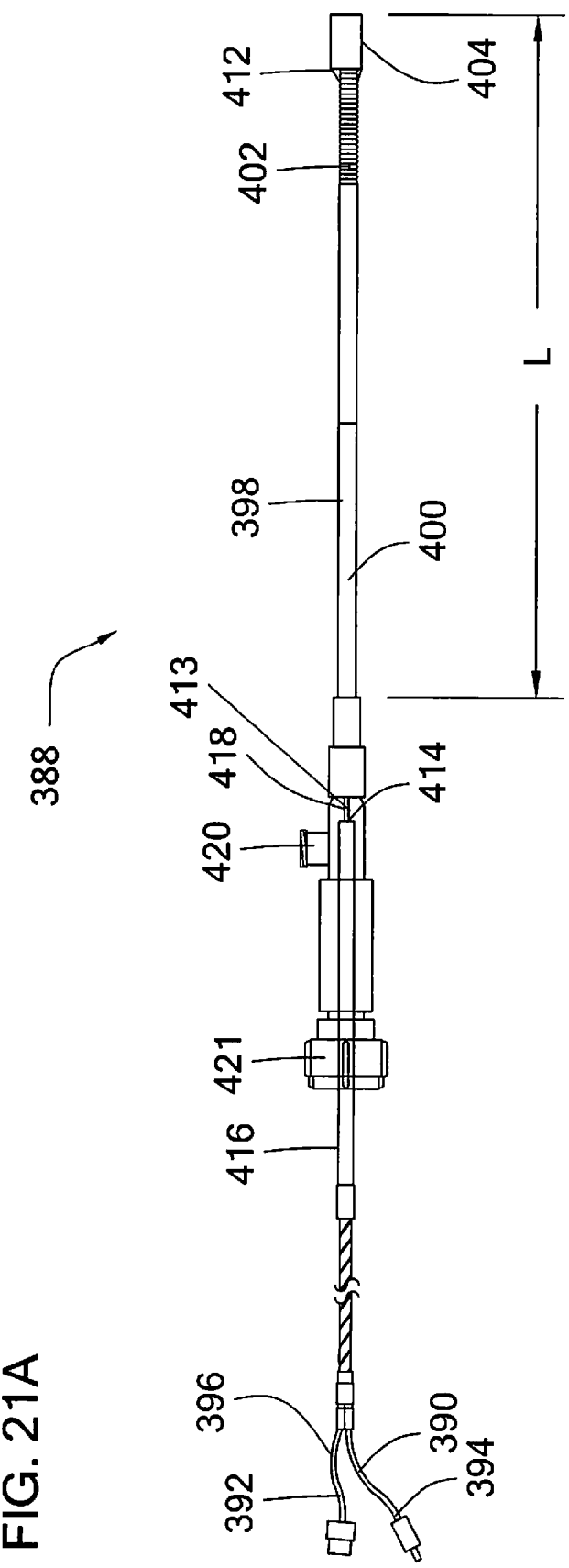
FIG. 21A side view of another embodiment of the coaxial bi-directional micro-endoscope of the present invention.
Figure 21C:
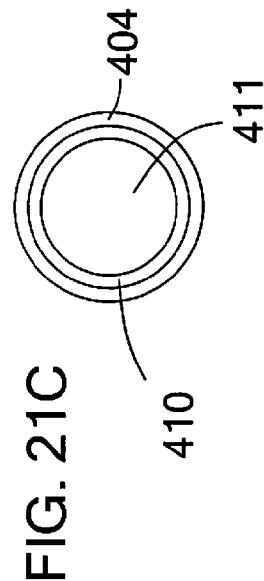
FIG. 21C is a front view of an alternate embodiment of the micro-endoscope.
Figure 21B:
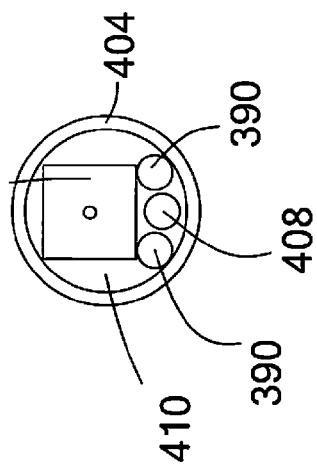
FIG. 21B is a front view of the micro-endoscope of FIG. 21A.
Figure 21D:
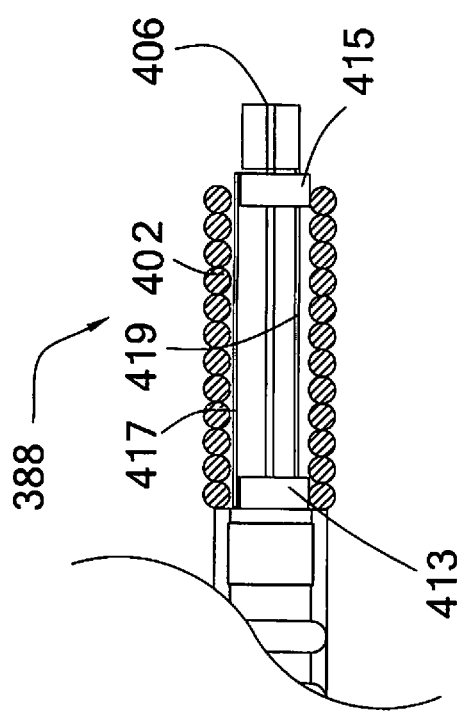
FIG. 21D is an enlarged view in partial cross section of the distal portion of the micro-endoscope of FIG. 21B.

FIGS. 21A, 21B, and 21D illustrate another embodiment of a coaxial bi-directional micro-endoscope 388 without a guidewire lumen to reduce the overall outer diameter of the distal tip as well as the overall device diameter. In this embodiment, the illumination fibers 390 and power and data cable 392 (located inside tubes 394 and 396, respectively) run through the center of the outer catheter body 398, which is made up of a variable stiffness shaft 400 and distal coil 402, and are covered distally by cover 404. The variable stiffness shaft 400 is reinforced and has a lubricious inner liner, similar to a microcatheter. The inner diameter of the outer catheter body is about 0.042" with an outer diameter of about 0.050". The distal coil 402 can be made of any material and may even be laser cut and/or covered in plastic to make air/liquid tight and contain an inner lubricious liner. If laser cut, cutting must be done so that bending is optimized. Also, the laser cut version of the cover can be part of a complete outer catheter body and not two separate parts, as shown. As shown in FIG. 21B, cover 404 covers CMOS camera assembly 406, illumination fibers 390, and a flush hole 408. The cover 404 can be made of a metal, polymide, plastic or other material or a coil with all components potted in epoxy or glue 410. Plastic tubing can also be shrunk down to create a cover using removable heat shrink tubing. In this case, the resulting tip may be oval more than round due to squeezing of the parts together. Glue or solder 412 can be used to create smooth transition between proximal end of cover 404 and distal end of distal coil 402.

The illumination fibers 390 and power and data cable 392 run inside a polyimide tube 413 with an inner diameter of about 0.034" and an outer diameter of about 0.040". The polyimide tube dimensions can vary so long as the illumination fibers and power and data cable can be snaked through the tube's inner diameter and tube movement is free relative to the inner diameter of the outer catheter body. Or, if desired, the parts can be held together by bands, glue, shrink tubing, other methods or even left free inside the outer catheter body. An optional stainless steel or other material wire can be added to the fibers and camera cable assembly to help with axial movement and tracking. The polyimide tube 413, which can be laser cut to help with flexibility, is positioned so that approximately 3 cm of the illumination fibers and the power and data cable with CMOS camera extend distally from the tube (not shown). A glue joint is formed at the polyimide distal end to form a bond between the tube, fibers, and cable (not shown). The polyimide tube 413 extends up to proximal end 414 where it is covered with stainless steel hypotube 416 and another glue joint is applied to bond everything together. A gap 418 of greater than about 2 mm is left so that tube 416 can be pushed distally to cause deflection due to the interaction of the column and overlying reinforcement tube or coil in the same manner as described above. Note, as stated above, the cover tube need not be polyimide, it can be made of any material or other methods can be used to hold components together so that they can be pushed and pulled.

Flushing liquid can be introduced through arm 420 and exits distally from flush port 408 at the very distal tip which can be formed in the adhesive of epoxy using a removable PTFE covered mandrel during manufacturing. Flush port 408 can be 0.008" or greater. Lock 421 is used to lock the deflectable tip in various positions. Deflection is brought about by pushing and pulling tube 416, which causes the fibers and data cable to deflect the distal tip based on the column theory described herein. A screw system can also be added to the proximal end so that rotation will move tube 416 and bring about tip deflection. This particular configuration may have a usable length L of approximately 5 cm or longer. Longer versions can act as guidewire like structures, which can be tracked through an opening, like Acclarent's Relieva Luma Sinus Illumination System, to provide direct visualization or to assist in placement/treatment.

In this particular embodiment, movement of the power and data cable as well as the illumination fibers results in deflection of the distal tip. In other words, the cable and fibers can be moved proximally or distally relative to outer catheter 337, and thereby effect deflection in the same manner as the axially moveable inner catheters described herein effect deflection due to the interaction of the column 370 and outer reinforcement coil 354 (or tube).

FIG. 21C illustrates the front view of a distal tip of another embodiment of a coaxial bi-directional micro-endoscope 388' without a guidewire lumen to reduce the overall outer diameter of the distal tip as well as the overall device diameter. In this embodiment, there is a single optical fiber 411 running through the catheter body (not shown). It is embedded in glue or epoxy 410 and covered with cover 404. The single fiber can be made of glass, quartz, or polymer and have dimensions of around 0.010" to 0.020". Alternatively, the single fiber can be a fiber optic bundle composed of many fibers or an LED. The uses of this structure can range from imaging, laser lithotripsy, or even lighting and can be used in fields such as ENT, GI and urology. Depending on use, the proximal fittings will be required to change to fit necessary capital equipment (not shown). The above dimensions and construction are purely exemplary and are not limiting in any way to final device design. The fiber 411 can be used to deflect the tip by axial proximal and distal movement under the column theory described herein. The fiber diameter can range from less than 1 micron to greater than 600 microns.

FIG. 21D illustrates distal section 388 of FIG. 21A in partial cross section. As shown in FIG. 21D, power and data cable 419 and fiber(s) 406 run through band 415 and band 413 where they enter the outer catheter. Not shown in the partial cross section are glues, solders and marker band 404 that complete the distal tip assembly. Since glues are not shown, hole 408 which is formed in glue or adhesive 410 is not visible. Movement of power and data cables along with fibers will result in tip deflection.

Figure 21E:
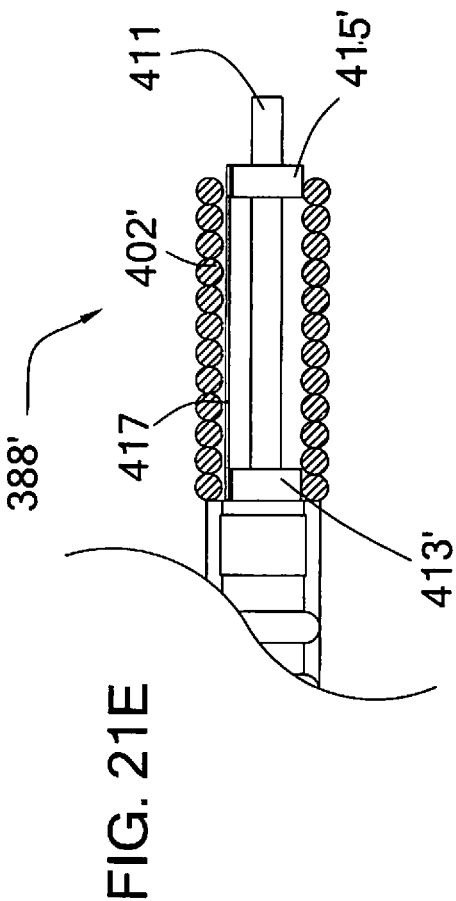
FIG. 21E is an enlarged view in partial cross section of the distal portion of the micro-endoscope of FIG. 21C.

FIG. 21E illustrates FIG. 21C in a partial cross section. In this embodiment, fiber 411 runs under band distal 419' and proximal band 413' and then enters the outer catheter. Not shown in the partial cross section are the glues, solder, and marker band 404 that complete the tip assembly. Movement of the fiber will result in tip deflection.

Figure 22:
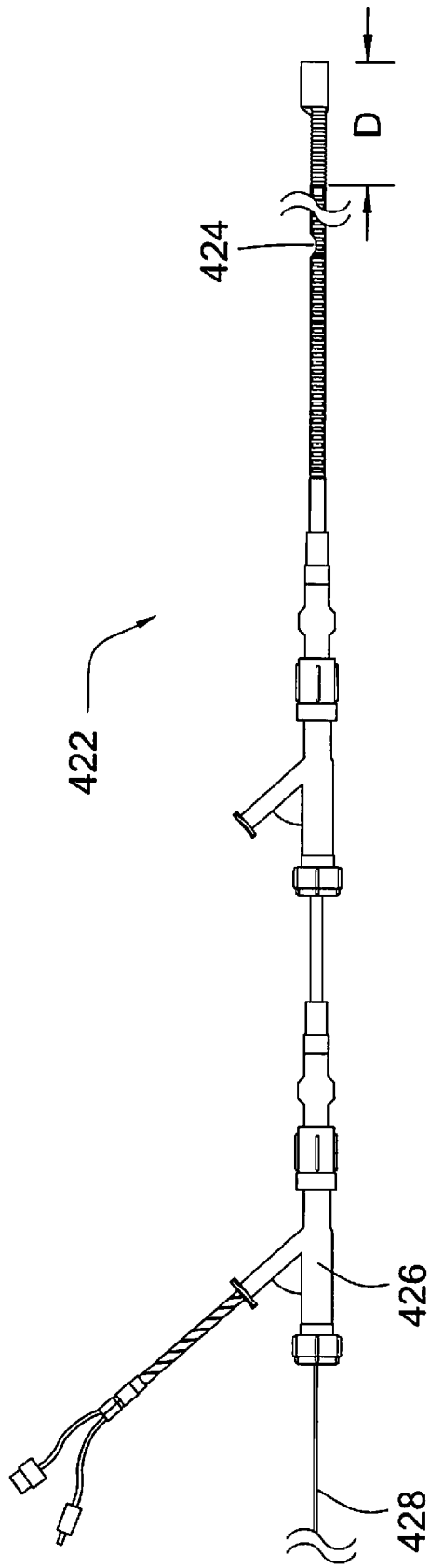
FIG. 22 is a side view of another embodiment of the coaxial bi-directional micro-endoscope of the present invention.
Figure 23:
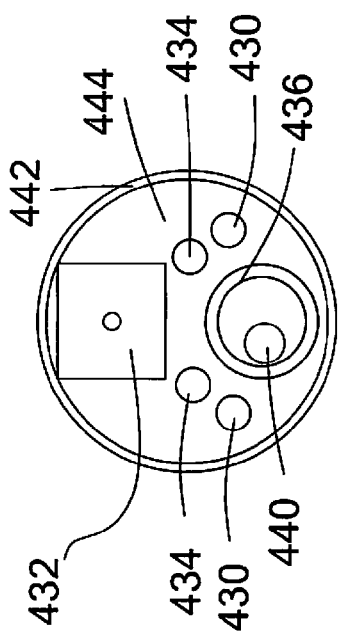
FIG. 23 is a front view of the micro-endoscope of FIG. 22.

A coaxial bi-directional micro-endoscope 422, similar in construction to coaxial bi-directional micro-endoscope 337 shown in FIGS. 20A through 20C with the exception of rapid exchange port 424 is illustrated in FIGS. 22 and 23. The purpose of the rapid exchange port is to allow a guidewire or other tool to be placed through the side of the inner lumen of the catheter for tracking or treatment. The rapid exchange port may be placed anywhere proximal of the deflecting section (D) of the catheter. The exact placement will depend on the distal tip bending radius used for design. In some instances, the port may be about 6 mm from the distal tip. Also, the length of the rapid exchange port cut on the inner catheter (not shown) may be longer than the cut on the outer catheter to accommodate deflection with guidewire in place. However, they can also be cut to the same length or the outer can be cut longer than the inner. Because the inner and outer catheters move relative to one another in this design, the rapid exchange ports must also be able to move relative to one another to accommodate deflection. If the guidewire or other device will not be deflected, the rapid exchange port can be placed in deflection section D. The provision of a rapid exchange port can be utilized in the other embodiments of the micro-endoscopes disclosed herein.

This particular design allows for introduction of other devices through the proximal end of the device. Shown extending from RHV 426 is an electrohydraulic lithotripsy (EHL) device 428, as made by Northgate Technologies, Inc. (Illinois). Other possible devices for insertion may include biopsy probes or guidewires, for example. Additional lighting in the form of fibers or LEDs may also be introduced through the inner lumen so as to help in illumination during camera use. A guidewire may also be combined with lighting so as to provide a tracking device in addition to lighting, as done by Acclarent in the Relieva Luma Sinus Illumination System. The rapid exchange version need not have an open lumen on the proximal end of the catheter, as shown. If desired, the design can be close ended and lithotripsy or other treatment option may be built into the catheter.

Lithotripsy wires (probes) 430 are embedded in the catheter distal tip. Also shown in the tip are the CMOS camera 432, illumination fibers 434, and inner catheter 436 containing guidewire 440. The components are covered by cover 442 and then glued in place using glue or epoxy 444. As stated early, the cover can be made out of plastic, metal or constructed using other standard methods for containing and manufacturing endoscope and catheter tips.

Figure 24A:
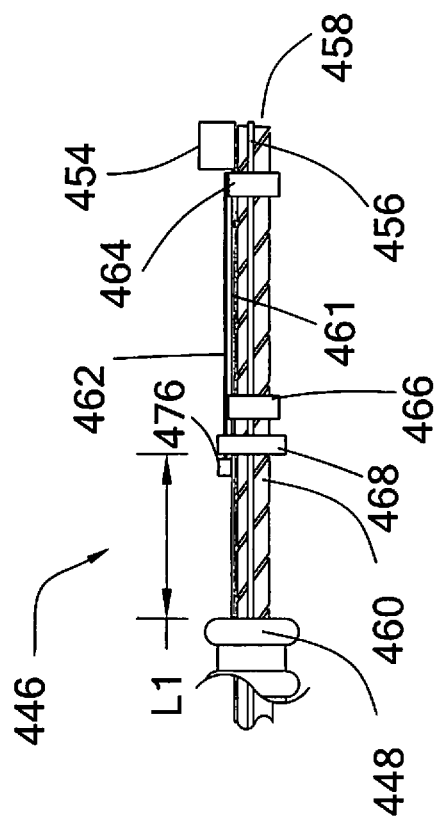
FIG. 24A is a side view of an alternate embodiment of the mechanism for deflecting the distal tip of the micro-endoscope with the lateral reinforcement tube removed for clarity.

FIG. 24A illustrates an alternate embodiment of the distal tip deflection mechanism 446. The design is meant to allow the inner shaft with attached components to rotate and deflect 360 degrees. This is achieved by attaching the column 462 only to the inner catheter and not attaching it to the outer catheter and thus the column does not attach both catheters. A portion L1 of the outer catheter 448, the outer coil 450, and cover 452 have been removed to show internal construction. As in earlier designs, the CMOS camera 454 and illumination fibers 456 run to the distal end 458 of the inner catheter 460 where they are mounted (glue or epoxy not shown). Although shown flush at the distal end, the fibers, camera, and catheter distal end can be staggered. In some cases, the camera may be mounted distal of the distal inner catheter tip while the fibers or other lighting method is proximal. Also, the inner catheter 460 is shown with a spiral tip however, as in other designs, the inner catheter can be a solid shaft. In that case, the shaft may have a lubricious inner liner, coil reinforcement and a variable stiffness shaft design. Column 462 is attached to distal marker band 464 and proximal marker band 466, as in some of the previous designs; however, a section of the column continues proximally where it passes under band 468 which would be glued in place. Attached at the proximal end of the column 462 is stop 476. This configuration will allow the column 462 to turn with the inner catheter body and attached components when it is torqued. If this design is used in combination with rapid exchange, the inner and outer exchange ports may become misaligned due to torquing. The reinforcement (support) tube and cover have been removed in FIG. 24A for clarity.

Figure 24B:
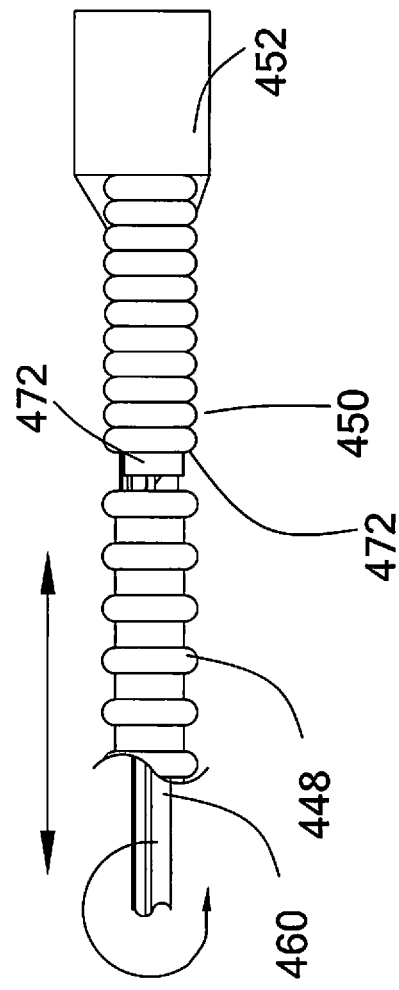
FIG. 24B is a side view of the mechanism for deflecting the distal tip of the micro-endoscope of FIG. 24A with the reinforcement tube shown.

FIG. 24B illustrates the tip deflection mechanism 446 with outer catheter 448, distal outer (reinforcement) coil 450 and cover 452 in place and in use. The inner catheter 460 can be rotated causing the column 462, which is now part of the inner catheter 460, to rotate which allows 360 degree deflection because it can deflect in any plane. When the outer catheter 448 is advanced, or the inner catheter 460 retracted, the other catheter 448 will make contact with end 472 and further movement will cause the tip to deflect. If the outer catheter 448 is pulled proximally or the inner catheter 460 is advanced, stop 476 contacts the outer catheter 448 and continued movement will cause the catheter to deflect in the opposite direction.

FIG. 25 shows a coaxial bi-directional micro-endoscope 388 without a guidewire lumen and fitted with rotational control system 474. Rotational control system 474 consists of stainless steel hypotube 476, which has been flattened in a region to create distal stop 478 and proximal stop 480, and ovalized or flattened hypotube 482, which in turn is soldered to stainless steel hypotube 484 which is dimensioned to fit inside tube 488. Glue 486 is used to lock the assembly in place inside tube 490.

In use, stainless steel hypotube 476 will be allowed to move axially to deflect the distal tip in accordance with the column/reinforcement tube structures described herein. Hypotube 476 moves axially distally and proximally until stops 478 and 480 are reached. Rotation of hypotube 476 will be restricted due to flattened region and ovalized hypotube 482 through which it freely moves. The rotational control concept can be used on designs without a guidewire lumen (as shown here), designs with a guidewire lumen (rapid exchange or other), or in any design that requires pure axial movement with little to no rotation. In addition, although this design uses flattened hypotubes, the concept can be injection molded into parts such as rotation hemostasis valves (RHV) to quicken manufacturing.

FIG. 26 illustrates an embodiment of a coaxial bi-directional micro-endoscope direct visualization system 492 using fiber optic illumination. Visualization system 490 includes coaxial bi-directional micro-endoscope 494 with illumination cable 496 and power and data cable 498, interface board (controller) 500, and light source 502. The illumination cable 496 is plugged into light source 502 which in turn is plugged into electrical plug 504. The light source can be fitted with LED lighting or other light source used for illuminating endoscope illumination fibers. Also, light source may be battery powered. The power and data cable 498 is plugged into interface board 500, which is then plugged into a computer 506 or other video imaging system with USB cord 508. The computer is loaded with the visualization software.

Although the interface board (controller) and light source are shown as separate units, they can be combined into a single unit that can be plugged into the computer or optionally made wireless box using an internal WIFI connection (board). Also, the light source can be fitted with a foot pedal or handle to allow for increasing or decreasing light source intensity, which would be normally controlled at the light source box, with press of pedal or button. The light source in other designs may also be incorporated into the catheter as part of the handle, making it disposable.

Once the visualization system is ready, a guidewire 493 is inserted through the working channel of coaxial bi-directional micro-endoscope 494 and the combined assembly is inserted into the working channel of a larger endoscope for tracking to the area of interest inside the body. Alternatively, the micro-endoscope can be tracked over a guidewire that is already in place in the body using either the rapid exchange or full inner lumen version.

Once the micro-endoscope is in place, images can be viewed and recorded. If needed, the working channel of the micro-endoscope can be used for diagnostic and/or therapeutic procedures once the guidewire is removed. When the end cap on the outer catheter's RHV is open, movement of the inner catheter body will result in deflection. Irrigation and/or insufflation can be introduced through the side arm on the outer catheter RHV. After the procedure is completed, the device is removed and the coaxial bi-directional micro-endoscope 494 can be discarded or in alternate embodiments resterilized. The interface board, light source or combined WIFI system can be reusable.

Although interface board 500 is shown connected to a computer 506 using USB connector and cable 508, other connectors and formats can be used, for instance NTSC or PAL to connect to other viewing options so long as they have the appropriate software. In addition, an IPad, IPhone (cell phone), or other device may be used for viewing if the catheter system is configured with WIFI. The steps described above for preparation and use of the coaxial bi-direction micro-endoscope are only an example of how the scope can be prepared and used. They are not meant to be the standard. For instance, the guidewire may be optionally left out if tracking is not required of the device or the coaxial bi-directional micro-endoscope can be used as a standalone device not requiring another endoscope.

FIG. 27 illustrates a distal portion of a coaxial micro-endoscope 510 fitted with distal balloon 512, such as an angioplasty balloon. The catheter is non-deflectable and the camera and lighting 514 are seated proximal to the balloon. Inflation ports 516 are used for inflation of the balloon. Alternatively, the camera and lighting can be placed distal of the balloon, if needed, in which case they would be mounted on the inner shaft or between distal and proximal balloons. The catheter design can be over-the-wire, rapid exchange, or non-over-the wire, depending on need. Hydrophilic coatings may be added to help with tracking.

FIG. 28 illustrates a distal portion of a coaxial micro-endoscope 518 with a pre-formed distal portion 520. Forming can be done using steam in the operating room, as done in interventional neuroradiology or at manufacturing facility. Pre-shaped devices may be useful in parts of the body where a short device is used, allowing easy rotation of the catheter for a 360 degree view. Placing a stiff wire through the center lumen can change the angle 522 of the pre-formed tip by straightening the tip out. If desired, a rapid exchange port can be cut in the side of the catheter and coatings can be added. Lastly, catheters up to now have been fitted with a single, forward facing camera. It is understood that cameras can be mounted at different angles or directions on the shaft and stereo cameras, as produced by Awaiba (Germany) may be used.

Note the dimensions and ranges provided herein are given by way example, it being understood that other dimensions and ranges for the components described herein are also contemplated.

The deflection of the micro-endoscope of the present invention can be summarized as follows. Bi-directional deflection of the distal tip of the micro-endoscope can be broken down into two distinct motions: axial pull deflection and axial push deflection. Axial pull deflection can be modeled as an eccentrically loaded column while axial push deflection can be modeled as an eccentrically loaded beam.

With respect to axial pull deflection, when no lateral support tube is present on the distal end of the micro-endoscope, the rectangular nitinol wire (or alternate column member structure such as a rod discussed above) is modeled as an unsupported eccentrically loaded column. This means that when the inner catheter is moved axially proximal with a force P in the proximal direction, the distal end of the column (rectangular nitinol wire) will want to move axially toward its proximal end, resulting in compression (buckling) of the nitinol wire. This is shown in FIG. 6C which illustrates movement of the column 121 in the absence of the lateral support tube to explain the tip concept of the present invention. With the lateral support tube (e.g., coil) provided and the inner catheter is again pulled axially with a force P in the proximal direction, the column (e.g., rectangular nitinol wire) will attempt to compress (buckle) axially however it will be restricted by the lateral reinforcement tube, e.g., tube 125. Since the tip can no longer fail axially (in compression), it will fail laterally (deflect) (see FIGS. 6D and 6E).

It should be appreciated that axial proximal movement of the inner catheter is discussed. However, it should be appreciated that distal movement of the outer catheter would achieve the same effect. Therefore, as used herein, relative movement includes movement of the inner catheter with respect to the outer catheter, movement of the outer catheter with respect to the inner catheter, or movement of both in opposite directions with respect to each other.

With respect to axial push deflection, when no lateral support tube is present on the distal end of the micro-endoscope, the rectangular nitinol wire (or alternate column member structure such as a rod discussed above) is modeled as an eccentrically loaded beam. This means that when the inner shaft is pushed axially with a force P it will apply a moment to the end of the beam (rectangular nitinol wire), which causes it to bend (see FIG. 6F). When the lateral support tube (e.g., coil) is provided and the inner catheter is pushed axially with a force P in the distal direction, there will be a moment applied to the overall tip causing it to bend (deflect) as shown in FIG. 6G and FIG. 6H. In this case, the addition of the coil does not change the action, it simply keeps the components together. It should be appreciated that axial distal movement of the inner catheter is discussed. However, it should be appreciated that proximal movement of the outer catheter would achieve the same effect. Therefore, as used herein, relative movement includes movement of the inner catheter with respect to the outer catheter, movement of the outer catheter with respect to the inner catheter, or movement of both in opposite directions with respect the each other.

Axial pushing and pulling can be considered in terms of an x-y axis. Axial pushing and pulling will happen on the x axis and bending (deflection) will end up in at a point (x,y). So for compression of column causing the tip to bend to the y1 position, the distal end of the tip is traveling in the −x1 direction towards its proximal end (−x2).

Thus, as can be appreciated, in the coaxial catheter arrangement of the present invention, deflection of the distal tip is achieved by an axial motion, rather than a pulling down on the distal tip as in prior art non-coaxial catheters. Thus, the micro-endoscope itself is being used to bend the distal tip as opposed to the prior art side by side wire and catheter. Viewed in another way, the bending is achieved not by pulling in the direction of bending but by an axial movement. The structure of the coaxial bi-directional micro-endoscope of the present invention saves space to reduce the overall size (diameter) of the micro-endoscope to provide a reduced profile for insertion. It also provides space for fluid flow to enhance deflection (by enhancing relative movement of the inner and outer catheters) without requiring an increase in the size (diameter) of the micro-endoscope. As explained above, the coaxial bi-directional micro-endoscope can be used with the CMOS sensor technology or with other visualized systems. It is also contemplated that the CMOS sensor or other visualization-system can be mounted on the inner shaft.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A deflectable endoscope comprising:
    an imaging structure;
    a longitudinally extending elongated outer member having a proximal portion and a distal portion having a distalmost end;
    an elongated column member extending distally from the outer member and distal of the distalmost end of the outer member;
    an inner member positioned coaxial with the outer member and attached to the column member, the inner member extending distally of the distalmost end of the outer member and having a distal tip portion; and
    a reinforcement member positioned over the column member to restrict axial movement of the column member such that when one of the inner member or outer member is moved coaxially with respect to the other, axial compression of the column member is restricted by the reinforcement member causing the distal tip portion of the inner member to deflect laterally, wherein the distal tip portion is deflectable in a first direction with respect to a longitudinal axis in response to a first direction of axial movement of one of the inner member or outer member and the distal tip portion is deflectable in a second direction with respect to the longitudinal axis in response to a second different direction of axial movement of one of the inner member or outer member.

2. The deflectable endoscope of claim 1, wherein the outer member has a central longitudinal axis and the column member along its entire length is radially offset with respect to the central longitudinal axis of the outer member, the column member positioned external of the inner member.

3. The deflectable endoscope of claim 1, wherein the reinforcement member comprises a tube.

4. The deflectable endoscope of claim 1, wherein the column member is non-circular in cross-section.

5. The deflectable endoscope of claim 1, wherein the column member is fixedly attached at one end to the outer member and at an opposite end to the inner member.

6. The deflectable endoscope of claim 1, wherein the outer member has a central lumen to receive the inner member and the inner member has a central lumen to receive a guidewire therethrough for tracking of the endoscope thereover.

7. The deflectable endoscope of claim 1, wherein the column member has a proximal portion attached to the distal portion of the outer member and a distal portion attached to a distal portion of the inner member.

8. The deflectable endoscope of claim 1, wherein upon movement of the inner member proximally or movement of the outer member distally, the axial compression of the column member is limited by the reinforcement member so it cannot fail axially but instead fails laterally to deflect the distal tip portion.

9. The deflectable endoscope of claim 1, wherein the central lumen of the outer member is lubricated to facilitate movement of the inner member therein.

10. The deflectable endoscope of claim 1, further comprising a locking assembly to lock the position of the inner member with respect to the outer member.

11. The deflectable endoscope of claim 1, wherein the imaging structure is attached to the outer member and does not deflect with the distal tip portion.

12. The deflectable endoscope of claim 1, wherein the imaging structure is fixedly attached to the inner member and deflects with the distal tip portion.

13. The deflectable coaxial catheter of claim 1, wherein the column member is external of the inner member.

14. A deflectable coaxial catheter comprising:
   an inner catheter;
      an outer catheter positioned coaxially over the inner catheter wherein relative coaxial movement of the inner and outer catheters deflects a distal tip portion of the coaxial catheter in first and second directions with respect to a longitudinal axis of the coaxial catheter, wherein the distal tip portion is deflectable in the first direction with respect to the longitudinal axis in response to a first direction of axial movement of one of the inner catheter or outer catheter and the distal tip portion is deflectable in the second direction with respect to the longitudinal axis in response to a second different direction of axial movement of one of the inner catheter or outer a column member extending between the inner and outer catheters and external of the inner catheter; and
   an imaging structure carried by one or both of the inner catheter and outer catheter; wherein buckling of the column member is restricted by a reinforcement member so the column member fails axially in response to the first direction of axial movement of one of the inner catheter or outer catheter.

15. The deflectable coaxial catheter of claim 14, wherein the imaging structure is proximal of the deflecting distal tip portion.

16. The deflectable coaxial catheter of claim 14, wherein the imaging structure is attached to the deflecting distal tip portion.

17. The deflectable coaxial catheter of claim 14, wherein the imaging structure is mounted on an outer surface of one or both of the outer catheter and inner catheter.

18. The deflectable coaxial catheter of claim 14, wherein the inner catheter has a lumen to receive a guidewire therethrough for tracking of the endoscope thereover.

* * * * *